(12) United States Patent
Estabrook et al.

(10) Patent No.: US 8,877,479 B2
(45) Date of Patent: Nov. 4, 2014

(54) HALOMONAS STRAIN WDG195-RELATED ALPHA-AMYLASES, AND METHODS OF USE, THEREOF

(75) Inventors: Melodie Estabrook, Mountain View, CA (US); Brian E. Jones, Leidschendam (NL); Marc Kolkman, Oegstgeest (NL); Chris Leeflang, GA Twisk (NL); Leo P. M. Van Marrewijk, Zoetermeer (NL)

(73) Assignee: Danisco US Inc., Palo Alto, CA (US)

( * ) Notice: Subject to any disclaimer, the term of this patent is extended or adjusted under 35 U.S.C. 154(b) by 299 days.

(21) Appl. No.: 13/263,312

(22) PCT Filed: Feb. 25, 2010

(86) PCT No.: PCT/US2010/025368
§ 371 (c)(1),
(2), (4) Date: Nov. 17, 2011

(87) PCT Pub. No.: WO2010/117511
PCT Pub. Date: Oct. 14, 2010

(65) Prior Publication Data
US 2012/0171748 A1    Jul. 5, 2012

Related U.S. Application Data

(60) Provisional application No. 61/167,612, filed on Apr. 8, 2009.

(51) Int. Cl.
*C12P 21/06* (2006.01)
*C12N 9/00* (2006.01)
*C12N 9/28* (2006.01)
*C11D 3/386* (2006.01)
*C07H 21/04* (2006.01)

(52) U.S. Cl.
CPC .......... *C11D 3/38681* (2013.01); *C12N 9/2417* (2013.01); *C11D 3/386* (2013.01)
USPC .......... 435/202; 435/69.1; 435/183; 510/226; 536/23.2

(58) Field of Classification Search
None
See application file for complete search history.

(56) References Cited

U.S. PATENT DOCUMENTS

| | | |
|---|---|---|
| 4,106,991 A | 8/1978 | Markussen et al. |
| 4,435,307 A | 3/1984 | Barbesgaard et al. |
| 4,661,452 A | 4/1987 | Markussen et al. |
| 5,281,526 A | 1/1994 | Good et al. |
| 5,427,936 A | 6/1995 | Moeller et al. |
| 5,457,046 A | 10/1995 | Woldike et al. |
| 5,648,263 A | 7/1997 | Schulein et al. |
| 5,686,593 A | 11/1997 | Woldike et al. |
| 5,691,178 A | 11/1997 | Schulein et al. |
| 5,763,254 A | 6/1998 | Woldike et al. |
| 5,776,757 A | 7/1998 | Schulein et al. |
| 5,827,718 A | 10/1998 | Ishida et al. |
| 5,871,550 A | 2/1999 | Goedegebuur et al. |
| 5,942,431 A | 8/1999 | Yoneda et al. |
| 6,562,612 B2 | 5/2003 | Jones et al. |
| 2006/0014265 A1 | 1/2006 | Ferrari et al. |

FOREIGN PATENT DOCUMENTS

| | | |
|---|---|---|
| CA | 2202553 | 4/1997 |
| EP | 0218272 | 4/1987 |
| EP | 0238023 | 9/1987 |
| EP | 0238216 | 9/1987 |
| EP | 0258068 | 3/1988 |
| EP | 0305216 | 3/1989 |
| EP | 0331376 | 9/1989 |
| EP | 0407225 | 1/1991 |
| EP | 0495257 | 7/1992 |
| GB | 1372034 | 10/1974 |
| GB | 1483591 | 8/1977 |
| JP | 64/074992 | 3/1989 |
| WO | WO89/06270 | 7/1989 |
| WO | WO89/06279 | 7/1989 |
| WO | WO89/09259 | 10/1989 |
| WO | WO91/17243 | 11/1991 |
| WO | WO91/17244 | 11/1991 |
| WO | WO92/05249 | 4/1992 |
| WO | WO92/06154 | 4/1992 |
| WO | WO92/19708 | 11/1992 |
| WO | WO92/19709 | 11/1992 |
| WO | WO92/19729 | 11/1992 |
| WO | WO93/24618 | 12/1993 |
| WO | WO94/01541 | 1/1994 |
| WO | WO94/07998 | 4/1994 |
| WO | WO94/25578 | 11/1994 |
| WO | WO94/25583 | 11/1994 |
| WO | WO95/10602 | 4/1995 |
| WO | WO95/14783 | 6/1995 |
| WO | WO95/22615 | 8/1995 |
| WO | WO95/24471 | 9/1995 |
| WO | WO95/30744 | 11/1995 |
| WO | WO95/35381 | 12/1995 |
| WO | WO96/00292 | 1/1996 |
| WO | WO96/11262 | 4/1996 |
| WO | WO96/13580 | 5/1996 |
| WO | WO96/29397 | 9/1996 |
| WO | WO97/04079 | 2/1997 |
| WO | WO97/07202 | 2/1997 |
| WO | WO98/08940 | 3/1998 |
| WO | WO98/12307 | 3/1998 |
| WO | WO98/15257 | 4/1998 |

(Continued)

OTHER PUBLICATIONS

Chica et al. Curr Opin Biotechnol. Aug. 2005;16(4):378-84.*

(Continued)

*Primary Examiner* — Christian Fronda
(74) *Attorney, Agent, or Firm* — Danisco US Inc.

(57) ABSTRACT

Compositions and methods relating to an alpha-amylase enzyme obtained from *Halomonas variabilis* WDG195 are described.

10 Claims, 13 Drawing Sheets

(56) References Cited

FOREIGN PATENT DOCUMENTS

| WO | WO98/20115 | | 5/1998 |
|---|---|---|---|
| WO | WO98/20116 | | 5/1998 |
| WO | WO98/34946 | | 8/1998 |
| WO | WO99/01544 | | 1/1999 |
| WO | WO01/14629 | | 3/2001 |
| WO | WO01/34899 | | 5/2001 |
| WO | WO02/31124 | | 4/2002 |
| WO | WO 02/31124 | * | 4/2002 |
| WO | WO2005/056783 | | 6/2005 |

OTHER PUBLICATIONS

Sen et al. Appl Biochem Biotechnol. Dec. 2007;143(3):212-23.*

Coronado, M.J. et al. "Production and biochemical characterization of an α-amylase from the moderate halophile *Halomonas meridiana*" *FEMS Microbiology Letters* 183: 67-71, 2000.

Coronado, M.J. et al., "The α-amylase gene *amyH* of the moderate halophile *Halomonas meridiana*: cloning and molecular characterization." *Microbiology* 146: 861-868, 2000.

Dang, H., et al., "Extracellular Hydrolytic enzyme screening of culturable heterotrophic bacteria from deep-sea sediments of the Southern Okinawa Trough." World Journal of Microbiology & Biotechnology 25(1): 71-79, 2009.

Dartois, V., et al., "Cloning, nucleotide sequence and expression in *Escherichia coli* of a lipase gene from *Bacillus subtilis* 168." *Biochemica et Biophysica Acta* 1131: 253-260, 1992.

Duckworth, A.W., et al., "Phylogenetic diversity of soda lake alkaliphiles." FEMS Microbiology Letters 19: 181-191, 1996.

GenBank Accession No. AJ239061, *Halomonas meridiana*, Coronado, M.J., et al., Apr. 15, 2005.

GenBank Accession No. CAB92963, *Halomonas meridiana*, Coronado, M.J., et al., Apr. 15, 2005.

Hagihari, H., et al. "Deduced amino-acid sequence of a calcium-free α-amylase from a strain of *Bacillus*." *Eur. J. Biochem.*(2001) 268:3974-82.

International Preliminary Report on Patentability of International Application No. PCT/US2010/025368 dated Oct. 11, 2011.

International Search Report and the Written Opinion of International Application No. PCT/US2010/025368 dated Jun. 4, 2010.

Nonaka, T. et al., "Crystal Structure of Calcium-free α-Amylase from *Bacillus* sp. Strain KSM-K38 (AmyK38) and Its Sodium Ion Binding Sites." *J. Biol. Chem.* 278:24818-23824, 2003.

* cited by examiner

```
                  10         20         30         40         50         60
                  |          |          |          |          |          |
AmyWDG195  EAENGTMMQYFEWHLENDGEHWNRMNVEAEALSEAGITALWIPPAYKGSGQGDVGYGAYD
AmySWT282  -MENGTMMQYYEWHLENDGEHWNRMNEQADDLADAGITALWIPPAYKGNSQQDVGYGAYD
AmyK38     DGLNGTMMQYYEWHLENDGQHWNRLHDDAAALSDAGITAIWIPPAYKGNSQADVGYGAYD
                *           *   **         *

70         80         90        100        110        120
                  |          |          |          |          |          |
AmyWDG195  LYDLGEFDQKGTVRTKYGTKAELESAIDEVQSQGIQVYGDVVMNHKMGADFTEAVEAVQV
AmySWT282  LYDLGEFDQKGTVRTKYGTKQELQNAVSSLQSEGLEVYGDVVLNHKMGADFTEAVDAVQV
AmyK38     LYDLGEFNQKGTVRTKYGTKAQLERAIGSLKSNDINVYGDVVMNHKMGADFTEAVQAVQV
                  *         *       *   *

130        140        150        160        170        180
                  |          |          |          |          |          |
AmyWDG195  NRSNRQQDISGAYEIEAWTGFDFPGRDGVYSDFQWRWFHFNGVDWDARYEEDHLFRLAHT
AmySWT282  NPDNRLQDISEAYTIDAWTGFTFEGRKNAYSDFNWHWYHFNGVDWDDRYGESHIFRLAHT
AmyK38     NPTNRWQDISGAYTIDAWTGFDFSGRNNAYSDFKWRWFHFNGVDWDQRYQENHIFRFANT
                                                                      * *

190        200        210        220        230        240
                  |          |          |          |          |          |
AmyWDG195  GWNSDVDLEYGNYDYLLGSNIDYSHPEVREEMMNWGSWFTDELNLDGYRLDAVKHVPAWY
AmySWT282  GWNHEVDTEKGNYDYLLGSNIDFSHPEVQDELKDWGSWYPEELNLDGYRIDAAKHIPFWY
AmyK38     NWNWRVDEENGNYDYLLGSNIDFSHPEVQDELKDWGSWFTDELDLDGYRLDAIKHIPFWY
              *

250        260        270        280        290        300
                  |          |          |          |          |          |
AmyWDG195  MNDWVGFQRDEADQDLFVVGEYWADDLGAIESYLERMDWDVSMFDVPLNYNFYEASRTGG
AmySWT282  ADDWVDHQRTEAGADQFVVSEYWIDDLGALENYLRELDWDVSVFDVPLNYNFYEASRTGG
AmyK38     TSDWVREQRNEADQDLFVVGEYWKDDVGALEFYLDEMNWEMSLFDVPLNYNFYRASQQGG
                                       *    * **              *    **

310        320        330        340        350        360
                  |          |          |          |          |          |
AmyWDG195  SYDMRNLLNGSLVEAHPMHAVTFVDNHDTQPGESLESWVDDWFKPLAYAVILTREGGYPS
AmySWT282  SYDMRNLLEGSLVEAHPQHAVTFVDNHDTQPGESLESWVDDWFKPLAYAVTLTREGGYPS
AmyK38     SYDMRNILRGSLVEAHPMHAVTFVDNHDTQPGESLESWVADWFKPLAYATILTREGGYPN
                *                                 *         *         *

370        380        390        400        410        420
                  |          |          |          |          |          |
AmyWDG195  VFYGDYYGIPNDGIGAKQDMLDTLLEARQDYAYGTQHDYFDHWDVVGWTREGSSSHPGSG
AmySWT282  VFYGDYYGIPNDNISAKKPMLDQLLEARTDYSYGTQHDYFDHWDIVGWTREGSTEVSGSG
AmyK38     VFYGDYYGIPNDNISAKKDMIDELLDARQNYAYGTQHDYFDHWDVVGWTREGSSSRPNSG
                               *    *   *                             *

430        440        450        460        470        480
                  |          |          |          |          |          |
AmyWDG195  MAAIMSNGPGGSKWMYVGSDRAGETWSDMTGNHGASVTINGDGWGEFHTDGGSVSIYTQQ
AmySWT282  LATLMSNGPGGSKWMYVGAQHAGDTWTDMLGNHSAQVTINQDGWGEFYTDGGAVSVYVQQ
AmyK38     LATIMSNGPGGSKWMYVGRQNAGQTWTDLTGNNGASVTINGDGWGEFFTNGGSVSVYVNQ
                                *  *                        *         *
```

*FIG. 7*

```
              1                                                    50
AmyK38    (1) DGLNGTMMQYYEWHLENDGQHWNRLHDDAAALSDAGITAIWIPPAYKGNS
AmySWT282 (1) -MENGTMMQYVEWHLENDGEHWNRTNEQADDLADAGITAIWIPPAYKGNS
AmyWDG195 (1) EAENGTMMQYFEWHLENDGEHWNRMNVEAEATSEAGITAIWIPPAYKGSG
Consensus (1) DAENGTMMQYYEWHLENDGEHWNRMNDDADALSDAGITALWIPPAYKGNS
              51                                                  100
AmyK38   (51) QADVGYGAYDLYDLGEFNQKGTVRTKYGTKAQERAIGSLKSNDENVYGD
AmySWT282(50) QQDVGYGAYDLYDLGEFLQKGTVRTKYGTKQELQNAVSSLQSELEVYGD
AmyWDG195(51) QGDVGYGAYDLYDLGEFLQKGTVRTKYGTKAELESADDEVLSQETQVYGD
Consensus(51) QADVGYGAYDLYDLGEFDQKGTVRTKYGTKAELE AI SLQSNGINVYGD
             101                                                 150
AmyK38  (101) VVMNHKMGADFTEAVQAVQVNPTNRWDISGAYTIDAWTGFDFSGENAY
AmySWT282(100)VVLNHKMGADFTEAVDAVQVNPDNRLQDISEAYTIDAWTGFTEGRKNAY
AmyWDG195(101)VVMNHKMGADFTEAVEAVQVNRSNRQQDISEAYETEAWTGFDPGRDGVY
Consensus(101)VVMNHKMGADFTEAVDAVQVNPSNR QDISGAYTIDAWTGFDF GR NAY
             151                                                 200
AmyK38  (151) SDFKWRWFHFNGVDWDQREQENHIFRFANTNWNWRVDEENGNYDYLLGSN
AmySWT282(150) SDFNWHWYHFNGVDWDRYGESHIFRELAHTGWNHEVDTEKGNYDYLLGSN
AmyWDG195(151) SDFQWRWFHFNGVDWDARYEEDHLFRLAHTGWNSDVDLEYGNYDYLLGSN
Consensus(151) SDFNWRWFHFNGVDWD RY E HIFRLAHTGWN DVD E GNYDYLLGSN
             201                                                 250
AmyK38  (201) IDFSHPEVQDELKDWGSWFTELDLDGYRLDAIKHIPFWTSDWVREQRN
AmySWT282(200) IDFSHPEVQDELKDWGSWYTERLNLDGYRIDAAKHIPEWYADDWVDHDRT
AmyWDG195(201) IDYSHPEVREEMMNWGSWFTEINLDGYRIDAVKHVPAWYMNDWVGFQRD
Consensus(201) IDFSHPEVQDELKDWGSWFTDELNLDGYRLDAIKHIPFWY  DWV HQR
             251                                                 300
AmyK38  (251) EADQDLFVVGEYWRDDVGALEFYLDEMNWEMSLFDVPLNYNFYRASQQGG
AmySWT282(250) EAGADQFVVSEYWIDDLGALENYLRSLDWDVSVFDVPLNYNFYRASRTGG
AmyWDG195(251) EADQDLFVVGEYWADDLGAIESYLERMDWDVSMFDVPLNYNFYEASRTGG
Consensus(251) EADQDLPVVGEYW DDLGALE YLDEMDWDVSLFDVPLNYNFYEASRTGG
             301                                                 350
AmyK38  (301) SYDMRNILRGSLVEAHPMHAVTFVDNHDTQPGESLESWVADWFKPLAYAT
AmySWT282(300) SYDMRNILEGSLVEAHPQHAVTFVDNHDTQPGESLESWVDDWFKPLAYAV
AmyWDG195(301) SYDMRNILNGSLVEAHPMHAVTFVDNHDTQPGESLESWVDDWFKPLAYAV
Consensus(301) SYDMRNLL GSLVEAHPMHAVTFVDNHDTQPGESLESWVDDWFKPLAYAV
             351                                                 400
AmyK38  (351) ILTREGGYPNVFYGDYYGIPNDNISAKKDMIDELLDARQNYAYGTQEDYF
AmySWT282(350) TLTREGGYPSVFYGDYYGIPNDNISAKKPMLDQLLEARTDYSYGTQEDYF
AmyWDG195(351) ILTREGGYPSVFYGDYYGIPNDGIGAKQDMLDTLLEARQDYAYGTQHDYF
Consensus(351) ILTREGGYPSVFYGDYYGIPNDNISAKKDMLD LLEARQDYAYGTQHDYF
             401                                                 450
AmyK38  (401) DHWDVVGWTREGSSSRENSGIATIMSNGPGGSKWMYVGRQNAGQTWTDLT
AmySWT282(400) DHWDIVGWTREGSTEVSPSGIATLMSNGPGGSKWMYVGAQHAGDTWTDVL
AmyWDG195(401) DHWDVVGWTREGSSSHPGSGMAATMSNGPGGSKWMYVGSDRAGETWSDMT
Consensus(401) DHWDVVGWTREGSSS  PGSGLATIMSNGPGGSKWMYVGAQ AGDTWTDMT
             451                           480
AmyK38  (451) GNNGASVTINGDGWGEFTNGGSVSMYVNQ
AmySWT282(450) GNHSAQVTINQDGWGEFYTDGGAVSMYVQQ
AmyWDG195(451) GNHGASVTINGDGWGEFHTDGGSVSIYTQQ
Consensus(451) GNHGASVTINGDGWGEFHTDGGSVSVYVQQ
```

*FIG. 8*

SEQ ID NO: 1
    Amino acid sequence of AmyH from *Halomonas meridiana*
MCGPRLPPRP SGRGFTRVFA DTFVHLFEWQ WEDVAQECEN WLGPKGFKAV
QVSPPQEHIQ GDAWWTRYQP VSYQLESRSG SSEAFADMVQ RCNAAGVDVY
ADAVINHVAH GKGQGIAGSS YDSEALSYPH YQRDDFHEPC GIEQSDYAQN
AESVRQCQLV GLPDLNTSDP TVQSRIADYL DTLAALGVGG IRIDAAKHMA
PSDIAEILAQ VDAPLYAFQE VIDLGGEAIS ATEYQGTADI TEFRYGASLG
DIFNNQALAN LQQFGESPAL LPSEQAIVFT DNHDNQRGHG AGGSNILTHR
DDQLYRLANM FMLAWPYGYP KVMSSYAFSN SDQGPPQAPV YQQGEAQCGE
AWVCEHRWPE IANMVAFRQQ AEGAEITHWW DNGHHQIAFS REAQGFIAIN
REQQALTHTF QTDMADGRYQ NVTAEGQCIV VEDGQLTLSV PAMSAAALHV
GAPCPAS SEQ ID NO: 2
    Nucleotide sequence of [partial] 16S rRNA gene of strain WDG195
GGCYTAACAC ATGCAAGTCG AGCGGTAACA GGGGTAGCTT GCTACCCGCT
GACGAGCGGC GGACGGGTGA GTAATGCATA GGAATCTGCC CGGTAGTGGG
GGATAACCTG GGGAAACCCA GGCTAATACC GCATACGTCC TACGGGAGAA
AGGGGGCTTC GGCTCCCGCT ATTGGATGAG CCTATGTCGG ATTAGCTAGT
TGGTGAGGTA ATGGCTCACC AAGGCGACGA TCCGTAGCTG GTCTGAGAGG
ATGATCAGCC ACATCGGGAC TGAGACACGG CCCGAACTCC TACGGGAGGC
AGCAGTGGGG AATATTGGAC AATGGGCGGA AGCCTGATCC AGCCATGCCG
CGTGTGTGAA GAAGGCCTTC GGGTTGTAAA GCACTTTCAG CGAGGAAGAA
CGCCTAGTGG TTAATACCCA TTAGGAAAG SEQ ID NO: 3
    pRANGER-FW primer
CAT AAG ATT AGC GGA TCC TAC CTG SEQ ID NO: 4
    pRANGER-RV primer
CAG CTT GTC CAG CAG GGT TGT CCA C SEQ ID NO: 5
    WDG195_FW1 primer
CGAATATTGATTACAGTCATCCGGAAGTAC SEQ ID NO: 6
    WDG195_FW2 primer
GGATGCCCGTATGAAGAAGATCACC SEQ ID NO: 7
    WDG195_RV1primer
CCACGTTCATCCGGTTCCAGTGCTCTCC

*FIG. 9A*

SEQ ID NO: 8
    WDG195_RV2 primer
GATCAAATTCCCCAAGATCGTACAGG

SEQ ID NO: 9
    Nucleotide sequence of the amyWDG195 gene
ATGAAAAAGACGTTGCTGACTGGAATGGCGGTCTTCATGCTGATGCCGTCGGGTACGGC
GCTGGCGGAAGCGGAAAATGGCACGATGATGCAGTATTTTGAATGGCACCTCGAAAACG
ACGGAGAGCACTGGAACCGGATGAACGTGGAAGCTGAGGCGCTGAGTGAAGCTGGCATC
ACGGCACTCTGGATTCCGCCGGCTTACAAAGGATCCGGACAGGGGGATGTCGGCTACGG
AGCCTACGACCTGTACGATCTTGGGGAATTTGATCAAAAAGGAACCGTACGGACAAAAT
ACGGTACAAAAGCAGAGCTGGAATCAGCCATCGATGAAGTGCAGTCGCAAGGCATCCAG
GTATACGGCGACGTTGTCATGAATCACAAAATGGGAGCTGATTTTACAGAAGCAGTCGA
GGCGGTGCAGGTGAACCGTTCCAACCGGCAGCAGGACATTTCCGGTGCGTATGAAATTG
AAGCGTGGACCGGCTTCGACTTTCCGGGAAGGGACGGTGTTTATTCCGATTTTCAGTGG
CGCTGGTTTCATTTTAACGGCGTAGACTGGGATGCCCGCTATGAAGAAGATCACCTTTT
CCGGCTCGCACATACGGGGTGGAATTCCGATGTCGACCTGGAGTACGGCAACTACGATT
ACCTGCTTGGGTCGAATATTGATTACAGTCATCCGGAAGTACGGGAAGAAATGATGAAC
TGGGGCAGCTGGTTTACAGACGAGCTGAATCTCGACGGCTACCGGCTGGATGCGGTGAA
GCACGTGCCCGCCTGGTATATGAATGACTGGGTCGGCTTTCAGCGGGACGAAGCGGATC
AGGATCTGTTCGTCGTCGGTGAATACTGGGCGGACGACCTCGGTGCAATTGAGAGCTAT
CTGGAGCGGATGGACTGGGACGTCTCCATGTTCGACGTGCCGCTGAACTATAATTTTTA
TGAAGCGTCGAGAACAGGCGGCAGCTACGATATGCGGAACCTGCTGAACGGCTCGCTCG
TTGAAGCGCATCCGATGCATGCGGTGACGTTTGTCGACAATCACGACACGCAGCCGGGA
GAATCGCTGGAGTCGTGGGTGGACGACTGGTTCAAGCCGCTTGCCTACGCCGTTATTCT
GACGCGTGAAGGCGGCTATCCGTCTGTCTTTTACGGGGATTACTACGGGATTCCGAACG
ACGGTATCGGCGCCAAGCAGGACATGCTCGATACGCTGCTGGAAGCAAGGCAGGACTAT
GCCTACGGCACCCAGCATGACTACTTTGACCATTGGGATGTGGTCGGCTGGACGCGTGA
AGGAAGCAGCAGCCACCCTGGTTCCGGCATGGCGGCCATTATGTCCAACGGCCCCGGCG
GATCGAAGTGGATGTACGTCGGCAGCGACCGGGCCGGGGAAACGTGGAGCGATATGACG
GGTAATCACGGCGCGTCTGTCACGATAAACGGAGACGGCTGGGGTGAATTCCATACGGA
CGGCGGATCCGTATCGATTTATACGCAGCAATAA SEQ ID NO: 10
    Amino acid sequence of the AmyWDG 195 precursor
MKKTLLTGMAVFMLMPSGTALAEAENGTMMQYFEWHLENDGEHWNRMNVEAEALSEAGI
TALWIPPAYKGSGQGDVGYGAYDLYDLGEFDQKGTVRTKYGTKAELESAIDEVQSQGIQ
VYGDVVMNHKMGADFTEAVEAVQVNRSNRQQDISGAYEIEAWTGFDFPGRDGVYSDFQW
RWFHFNGVDWDARYEEDHLFRLAHTGWNSDVDLEYGNYDYLLGSNIDYSHPEVREEMMN
WGSWFTDELNLDGYRLDAVKHVPAWYMNDWVGFQRDEADQDLFVVGEYWADDLGAIESY
LERMDWDVSMFDVPLNYNFYEASRTGGSYDMRNLLNGSLVEAHPMHAVTFVDNHDTQPG
ESLESWVDDWFKPLAYAVILTREGGYPSVFYGDYYGIPNDGIGAKQDMLDTLLEARQDY
AYGTQHDYFDHWDVVGWTREGSSSHPGSGMAAIMSNGPGGSKWMYVGSDRAGETWSDMT
GNHGASVTINGDGWGEFHTDGGSVSIYTQQ SEQ ID NO: 11
    Amino acid sequence of the AmyWDG195 signal peptide
MKKTLLTGMAVFMLMPSGTALA

FIG. 9B

SEQ ID NO: 12
    Amino acid sequence of mature AmyWDG195
EAENGTMMQYFEWHLENDGEHWNRMNVEAEALSEAGITALWIPPAYKGSGQGDVGYGAY
DLYDLGEFDQKGTVRTKYGTKAELESAIDEVQSQGIQVYGDVVMNHKMGADFTEAVEAV
QVNRSNRQQDISGAYEIEAWTGFDFPGRDGVYSDFQWRWFHFNGVDWDARYEEDHLFRL
AHTGWNSDVDLEYGNYDYLLGSNIDYSHPEVREEMMNWGSWFTDELNLDGYRLDAVKHV
PAWYMNDWVGFQRDEADQDLFVVGEYWADDLGAIESYLERMDWDVSMFDVPLNYNFYEA
SRTGGSYDMRNLLNGSLVEAHPMHAVTFVDNHDTQPGESLESWVDDWFKPLAYAVILTR
EGGYPSVFYGDYYGIPNDGIGAKQDMLDTLLEARQDYAYGTQHDYFDHWDVVGWTREGS
SSHPGSGMAAIMSNGPGGSKWMYVGSDRAGETWSDMTGNHGASVTINGDGWGEFHTDGG
SVSIYTQQ SEQ ID NO: 13
    Primer PstI-Amy195-I-Fw
CATT*CTGCAG*CTTCAGCAGAAGCGGAAAATGGCACGATGATGC SEQ ID NO: 14
    Primer HpaI-Amy195-Rv
CCTCT*GTTAAC*TTATTGCTGCGTATAAATCGATAC SEQ ID NO: 15
    pHPLT-F1 primer
TACATATGAGTTATGCAGTTTG SEQ ID NO: 16
    pHPLT-R1 primer
GTTATGAGTTAGTTCAAATTCG SEQ ID NO: 17
    Primer Amy195.int.-Rv
CTCCAGATAGCTCTCAATTGCACCGAG SEQ ID NO: 18
    Partial AmySWT282 coding sequence
AAAATGGGTGCTGATTTCACCGAAGCGGTGGATGCGGTGCAGGTGAATCCGGATAACCG
TCTGCAAGACATTTCGGAAGCTTACACGATCGACGCTTGGACAGGCTTTACATTTGAAG
GACGCAAGAACGCCTATTCGGATTTTAACTGGCACTGGTACCATTTTAACGGCGTAGAC
TGGGATGACCGGTATGGGGAAAGCCACATTTTCCGCCTGGCACATACCGGATGGAATCA
TGAAGTGGACACAGAGAAGGGGAATTATGATTATCTTCTCGGCTCGAATATCGATTTCA
GCCATCCCGAGGTGCAGGACGAGCTGAAAGACTGGGGAAGCTGGTATACAGAGGAATTA
AACCTGGACGGTTACCGGATTGATGCGGCTAAACATATTCCGTTCTGGTATGCTGATGA
CTGGGTCGATCACCAGCGTACAGAAGCCGGAGCGGATCAGTTTGTCGTCAGTGAATACT
GGATAGATGATCTTGGAGCACTCGAGAATTATTAAGAGAACTGGACTGGGACGTCTCC
GTGTTTGACGTGCCGCTGAACTACAATTTTTATGAGGCATCCCGCACCGGGGGAAGCTA
CGATATGCGGAATCTGCTGGAAGGGTCGCTTGTAGAAGCACATCCACAGCATGCG

*FIG. 9C*

SEQ ID NO: 19
  Nucleotide sequence encoding the AmySWT282 polypeptide precursor
ATGAAGAAACGATATGCTGGATTGCTTGTGCTGAGCGGATTGCTTTTGCCAACGGCAGG
AGTCTCTGCGATGGAGAACGGAACGATGATGCAGTATTACGAGTGGCATCTGGAAAACG
ACGGGGAGCATTGGAACCGAATGAATGAGCAGGCGGATGATTTAGCGGATGCTGGTATT
ACGGCGTTATGGATCCCCCCGGCCTATAAAGGGAACAGCCAGCAAGACGTCGGCTATGG
TGCCTATGACTTGTATGATTTAGGAGAATTTGACCAAAAAGGAACGGTGCGCACGAAGT
ACGGCACAAAGCAGGAGCTGCAGAACGCAGTGTCTTCACTGCAGTCGGAAGGGCTGGAG
GTATACGGAGATGTCGTTTTGAATCACAAAATGGGTGCTGATTTCACCGAAGCGGTGGA
TGCGGTGCAGGTGAATCCGGATAACCGTCTGCAAGACATTTCGGAAGCTTACACGATCG
ACGCTTGGACAGGCTTTACATTTGAAGGACGCAAGAACGCCTATTCGGATTTTAACTGG
CACTGGTACCATTTTAACGGCGTAGACTGGGATGACCGGTATGGGAAAGCCACATTTT
CCGCCTGGCACATACCGGATGGAATCATGAAGTGGACACAGAGAAGGGGAATTATGATT
ATCTTCTCGGCTCGAATATCGATTTCAGCCATCCCGAGGTGCAGGACGAGCTGAAAGAC
TGGGGAAGCTGGTATACAGAGGAATTAAACCTGGACGGTTACCGGATTGATGCGGCTAA
ACATATTCCGTTCTGGTATGCTGATGACTGGGTCGATCACCAGCGTACAGAAGCCGGAG
CGGATCAGTTTGTCGTCAGTGAATACTGGATAGATGATCTTGGAGCACTCGAGAATTAT
TTAAGAGAACTGGACTGGGACGTCTCCGTGTTTGACGTGCCGCTGAACTACAATTTTTA
TGAGGCATCCCGCACCGGGGAAGCTACGATATGCGGAATCTGCTGGAAGGGTCGCTTG
TAGAAGCACATCCACAGCATGCGGTCACGTTCGTGGACAATCATGATACGCAGCCGGGA
GAGTCGCTGGAGTCGTGGGTAGATGACTGGTTCAAACCACTTGCCTATGCGGTGACGCT
GACGAGAGAAGGCGGCTATCCAAGTGTTTTTTACGGGGATTACTACGGCATTCCGAACG
ACAACATCTCTGCGAAAAAACCAATGTTGGATCAGCTGCTGGAGGCACGCACGGATTAT
TCTTACGGCACACAGCACGATTATTTTGACCACTGGGATATCGTTGGTTGGACGAGAGA
AGGAAGCACAGAAGTGAGCGGCTCAGGACTTGCCACACTCATGTCCAATGGTCCAGGCG
GCTCCAAGTGGATGTATGTTGGAGCGCAGCACGCAGGAGACACCTGGACAGACATGCTC
GGAAATCACAGTGCGCAGGTGACAATTAATCAAGACGGCTGGGGAGAATTCTATACAGA
TGGCGGAGCCGTTTCTGTGTATGTCCAACAG SEQ ID NO: 20
  Nucleotide sequence encoding the mature AmySWT282 polypeptide
ATGGAGAACGGAACGATGATGCAGTATTACGAGTGGCATCTGGAAAACGACGGGGAGCA
TTGGAACCGAATGAATGAGCAGGCGGATGATTTAGCGGATGCTGGTATTACGGCGTTAT
GGATCCCCCCGGCCTATAAAGGGAACAGCCAGCAAGACGTCGGCTATGGTGCCTATGAC
TTGTATGATTTAGGAGAATTTGACCAAAAAGGAACGGTGCGCACGAAGTACGGCACAAA
GCAGGAGCTGCAGAACGCAGTGTCTTCACTGCAGTCGGAAGGGCTGGAGGTATACGGAG
ATGTCGTTTTGAATCACAAAATGGGTGCTGATTTCACCGAAGCGGTGGATGCGGTGCAG
GTGAATCCGGATAACCGTCTGCAAGACATTTCGGAAGCTTACACGATCGACGCTTGGAC
AGGCTTTACATTTGAAGGACGCAAGAACGCCTATTCGGATTTTAACTGGCACTGGTACC
ATTTTAACGGCGTAGACTGGGATGACCGGTATGGGAAAGCCACATTTTCCGCCTGGCA
CATACCGGATGGAATCATGAAGTGGACACAGAGAAGGGGAATTATGATTATCTTCTCGG
CTCGAATATCGATTTCAGCCATCCCGAGGTGCAGGACGAGCTGAAAGACTGGGGAAGCT
GGTATACAGAGGAATTAAACCTGGACGGTTACCGGATTGATGCGGCTAAACATATTCCG
TTCTGGTATGCTGATGACTGGGTCGATCACCAGCGTACAGAAGCCGGAGCGGATCAGTT
TGTCGTCAGTGAATACTGGATAGATGATCTTGGAGCACTCGAGAATTATTTAAGAGAAC
TGGACTGGGACGTCTCCGTGTTTGACGTGCCGCTGAACTACAATTTTTATGAGGCATCC
CGCACCGGGGAAGCTACGATATGCGGAATCTGCTGGAAGGGTCGCTTGTAGAAGCACA

FIG. 9D

```
TCCACAGCATGCGGTCACGTTCGTGGACAATCATGATACGCAGCCGGGAGAGTCGCTGG
AGTCGTGGGTAGATGACTGGTTCAAACCACTTGCCTATGCGGTGACGCTGACGAGAGAA
GGCGGCTATCCAAGTGTTTTTTACGGGGATTACTACGGCATTCCGAACGACAACATCTC
TGCCGAAAAAACCAATGTTGGATCAGCTGCTGGAGGCACGCACGGATTATTCTTACGGCA
CACAGCACGATTATTTTGACCACTGGGATATCGTTGGTTGGACGAGAGAAGGAAGCACA
GAAGTGAGCGGCTCAGGACTTGCCACACTCATGTCCAATGGTCCAGGCGGCTCCAAGTG
GATGTATGTTGGAGCGCAGCACGCAGGAGACACCTGGACAGACATGCTCGGAAATCACA
GTGCGCAGGTGACAATTAATCAAGACGGCTGGGGAGAATTCTATACAGATGGCGGAGCC
GTTTCTGTGTATGTCCAACAG
```

SEQ ID NO: 21
    AmySWT282 signal peptide coding sequence
```
ATGAAGAAACGATATGCTGGATTGCTTGTGCTGAGCGGATTGCTTTTGCCAACGGCAGG
AGTCTCTGCG
```

SEQ ID NO: 22
    AmySWT282 precursor amino acid sequence
```
MKKRYAGLLVLSGLLLPTAGVSAMENGTMMQYYEWHLENDGEHWNRMNEQADDLADAGI
TALWIPPAYKGNSQQDVGYGAYDLYDLGEFDQKGTVRTKYGTKQELQNAVSSLQSEGLE
VYGDVVLNHKMGADFTEAVDAVQVNPDNRLQDISEAYTIDAWTGFTFEGRKNAYSDFNW
HWYHFNGVDWDDRYGESHIFRLAHTGWNHEVDTEKGNYDYLLGSNIDFSHPEVQDELKD
WGSWYTEELNLDGYRIDAAKHIPFWYADDWVDHQRTEAGADQFVVSEYWIDDLGALENY
LRELDWDVSVFDVPLNYNFYEASRTGGSYDMRNLLEGSLVEAHPQHAVTFVDNHDTQPG
ESLESWVDDWFKPLAYAVTLTREGGYPSVFYGDYYGIPNDNISAKKPMLDQLLEARTDY
SYGTQHDYFDHWDIVGWTREGSTEVSGSGLATLMSNGPGGSKWMYVGAQHAGDTWTDML
GNHSAQVTINQDGWGEFYTDGGAVSVYVQQ
```

SEQ ID NO: 23
    AmySWT282 mature amino acid sequence
```
MENGTMMQYYEWHLENDGEHWNRMNEQADDLADAGITALWIPPAYKGNSQQDVGYGAYD
LYDLGEFDQKGTVRTKYGTKQELQNAVSSLQSEGLEVYGDVVLNHKMGADFTEAVDAVQ
VNPDNRLQDISEAYTIDAWTGFTFEGRKNAYSDFNWHWYHFNGVDWDDRYGESHIFRLA
HTGWNHEVDTEKGNYDYLLGSNIDFSHPEVQDELKDWGSWYTEELNLDGYRIDAAKHIP
FWYADDWVDHQRTEAGADQFVVSEYWIDDLGALENYLRELDWDVSVFDVPLNYNFYEAS
RTGGSYDMRNLLEGSLVEAHPQHAVTFVDNHDTQPGESLESWVDDWFKPLAYAVTLTRE
GGYPSVFYGDYYGIPNDNISAKKPMLDQLLEARTDYSYGTQHDYFDHWDIVGWTREGST
EVSGSGLATLMSNGPGGSKWMYVGAQHAGDTWTDMLGNHSAQVTINQDGWGEFYTDGGA
VSVYVQQ
```

SEQ ID NO: 24
    AmySWT282 signal peptide amino acid sequence
```
MKKRYAGLLVLSGLLLPTAGVSA
```

SEQ ID NO: 25
    Primer DVVMNH-Forward
```
GAYGTNGTNATGAAYCAY
```

*FIG. 9E*

SEQ ID NO: 26
    Primer VTFVDNHD-Reverse
TCRTGRTTITCIACRAANGTNAC

SEQ ID NO: 27
    Degenerate primer to the predicted N-terminal MMQ F/Y FEW conserved motif
ATGATGCARTWYTTYGARTGG-3'

SEQ ID NO: 28
    Primer to the C-terminal VTIN G/A DGWG E/N F motif
AAITYICCCCAICCRTCNSCRTTNGTNAC SEQ ID NO: 29
    Primer to the C-terminal NGGSVSVYVN motif
TTIACRAAIACISWIACISWICCNCCRTT SEQ ID NO: 30
    Primer N-Term SWT282 primer 2
CTAAATCATACAAGTCATAGGCACCATAGCCGAC SEQ ID NO: 31
    Primer N-Term SWT282 primer 1
GCAGCTCCTGCTTTGTGCCGTACTTCGTG SEQ ID NO: 32
    Primer C-term SWT282 primer 2 (SEQ ID NO: 32)
5'-GACCACTGGGATATCGTTGGTTGGACGAG SEQ ID NO: 33
    Primer C-term SWT282 primer 1 (SEQ ID NO: 33)
CACGCACGGATTATTCTTACGGCACACAG SEQ ID NO: 34
    AmyK38 full-length protein sequence (gi16874476)
    01 MRRWVAMLA VLFLFPSVVV ADGLNGTMMQ YYEWHLENDG QHWNRLEDDA AALSDAGITA
    61 IWIPPAYKGN SQADVGYGAY DLYDLGEFNQ KGTVRTKYGT KAQLERAIGS LKSNDINVYG
    121 DVVMNHKMGA DFTEAVQAVQ VNPTNRWQDI SGAYTIDAWT GFDFSGRNNA YSDFKWRWFH
    181 FNGVDWDQRY QENHIFRFAN TNWNWRVDEE NGNYDYLLGS NIDFSHPEVQ DELKDWGSWF
    241 TDELDLDGYR LDAIKHIPFW YTSDWVRHQR NEADQDLFVV GEYWKDDVGA LEFYLDEMNW
    301 EMSLFDVPLN YNFYRASQQG GSYDMRNILR GSLVEAHPMH AVTFVDNHDT QPGESLESWV
    361 ADWFKPLAYA TILTREGGYP NVFYGDYYGI PNDNISAKKD MIDELLDARQ NYAYGTQHDY
    421 FDHWDVVGWT REGSSSRPNS GLATIMSNGP GGSKWMYVGR QNAGQTWTDL TGNNGASVTI
    481 NGDGWGEFFT NGGSVSVYVN Q

*FIG. 9F*

SEQ ID NO: 35
    AmyK38 mature protein sequence
DGLNGTMMQ YYEWHLENDG QHWNRLHDDA AALSDAGITA
IWIPPAYKGN SQADVGYGAY DLYDLGEFNQ KGTVRTKYGT KAQLERAIGS LKSNDINVYG
DVVMNHKMGA DFTEAVQAVQ VNPTNRWQDI SGAYTIDAWT GFDFSGRNNA YSDFKWRWFH
FNGVDWDQRY QENHIFRFAN TNWNWRVDEE NGNYDYLLGS NIDFSHPEVQ DELKDWGSWF
TDELDLDGYR LDAIKHIPFW YTSDWVRHQR NEADQDLFVV GEYWKDDVGA LEFYLDEMNW
EMSLFDVPLN YNFYRASQQG GSYDMRNILR GSLVEAHPMH AVTFVDNHDT QPGESLESWV
ADWFKPLAYA TILTREGGYP NVFYGDYYGI PNDNISAKKD MIDELLDARQ NYAYGTQHDY
FDHWDVVGWT REGSSSRPNS GLATIMSNGP GGSKWMYVGR QNAGQTWTDL TGNNGASVTI
NGDGWGEFFT NGGSVSVYVN Q SEQ ID NO: 36
    Primer 282 N3
TACGCCGTTAAAATGGTACCAGTGCCAG SEQ ID NO: 37
    Primer 282 C1
CACGCACGGATTATTCTTACGGCACACAG SEQ ID NO: 38
    Primer 282 N5
ATTCACCTGCACCGCATCCACCGCTTCGG SEQ ID NO: 39
    Primer 282 C2
GACCACTGGGATATCGTTGGTTGGACGAG

SEQ ID NO: 40
    TOPO F
CACTTTATGCTTCCGGCTCGTATG

SEQ ID NO: 41
    Primer TOPO R
TCGCCATTCAGGCTGCGCAACTG

FIG. 9G

SEQUENCE LISTING

<160> NUMBER OF SEQ ID NOS: 42

<210> SEQ ID NO 1
<211> LENGTH: 457
<212> TYPE: PRT
<213> ORGANISM: Halomonas meridiana

<400> SEQUENCE: 1

```
Met Cys Gly Pro Arg Leu Pro Pro Arg Pro Ser Gly Arg Gly Phe Thr
1               5                   10                  15

Arg Val Phe Ala Asp Thr Phe Val His Leu Phe Glu Trp Gln Trp Glu
            20                  25                  30

Asp Val Ala Gln Glu Cys Glu Asn Trp Leu Gly Pro Lys Gly Phe Lys
        35                  40                  45

Ala Val Gln Val Ser Pro Pro Gln Glu His Ile Gln Gly Asp Ala Trp
    50                  55                  60

Trp Thr Arg Tyr Gln Pro Val Ser Tyr Gln Leu Glu Ser Arg Ser Gly
65                  70                  75                  80

Ser Ser Glu Ala Phe Ala Asp Met Val Gln Arg Cys Asn Ala Ala Gly
                85                  90                  95

Val Asp Val Tyr Ala Asp Ala Val Ile Asn His Val Ala His Gly Lys
            100                 105                 110

Gly Gln Gly Ile Ala Gly Ser Ser Tyr Asp Ser Glu Ala Leu Ser Tyr
        115                 120                 125

Pro His Tyr Gln Arg Asp Asp Phe His Glu Pro Cys Gly Ile Glu Gln
    130                 135                 140

Ser Asp Tyr Ala Gln Asn Ala Glu Ser Val Arg Gln Cys Gln Leu Val
145                 150                 155                 160

Gly Leu Pro Asp Leu Asn Thr Ser Asp Pro Thr Val Gln Ser Arg Ile
                165                 170                 175

Ala Asp Tyr Leu Asp Thr Leu Ala Ala Leu Gly Val Gly Gly Ile Arg
            180                 185                 190

Ile Asp Ala Ala Lys His Met Ala Pro Ser Asp Ile Ala Glu Ile Leu
        195                 200                 205

Ala Gln Val Asp Ala Pro Leu Tyr Ala Phe Gln Glu Val Ile Asp Leu
    210                 215                 220

Gly Gly Glu Ala Ile Ser Ala Thr Glu Tyr Gln Gly Thr Ala Asp Ile
225                 230                 235                 240

Thr Glu Phe Arg Tyr Gly Ala Ser Leu Gly Asp Ile Phe Asn Asn Gln
                245                 250                 255

Ala Leu Ala Asn Leu Gln Gln Phe Gly Glu Ser Pro Ala Leu Leu Pro
            260                 265                 270

Ser Glu Gln Ala Ile Val Phe Thr Asp Asn His Asp Asn Gln Arg Gly
        275                 280                 285

His Gly Ala Gly Gly Ser Asn Ile Leu Thr His Arg Asp Asp Gln Leu
    290                 295                 300

Tyr Arg Leu Ala Asn Met Phe Met Leu Ala Trp Pro Tyr Gly Tyr Pro
305                 310                 315                 320

Lys Val Met Ser Ser Tyr Ala Phe Ser Asn Ser Asp Gln Gly Pro Pro
                325                 330                 335

Gln Ala Pro Val Tyr Gln Gln Gly Glu Ala Gln Cys Gly Glu Ala Trp
            340                 345                 350
```

```
Val Cys Glu His Arg Trp Pro Glu Ile Ala Asn Met Val Ala Phe Arg
            355                 360                 365

Gln Gln Ala Glu Gly Ala Glu Ile Thr His Trp Trp Asp Asn Gly His
        370                 375                 380

His Gln Ile Ala Phe Ser Arg Glu Ala Gln Gly Phe Ile Ala Ile Asn
385                 390                 395                 400

Arg Glu Gln Gln Ala Leu Thr His Thr Phe Gln Thr Asp Met Ala Asp
                405                 410                 415

Gly Arg Tyr Gln Asn Val Thr Ala Glu Gln Cys Ile Val Val Glu
            420                 425                 430

Asp Gly Gln Leu Thr Leu Ser Val Pro Ala Met Ser Ala Ala Leu
        435                 440                 445

His Val Gly Ala Pro Cys Pro Ala Ser
    450                 455

<210> SEQ ID NO 2
<211> LENGTH: 429
<212> TYPE: DNA
<213> ORGANISM: Halomonas sp.

<400> SEQUENCE: 2
ggcytaacac atgcaagtcg agcggtaaca ggggtagctt gctacccgct gacgagcggc       60
ggacgggtga gtaatgcata ggaatctgcc cggtagtggg ggataacctg gggaaaccca      120
ggctaatacc gcatacgtcc tacgggagaa agggggcttc ggctcccgct attggatgag      180
cctatgtcgg attagctagt tggtgaggta atggctcacc aaggcgacga tccgtagctg      240
gtctgagagg atgatcagcc acatcgggac tgagacacgg cccgaactcc tacgggaggc      300
agcagtgggg aatattggac aatgggcgga agcctgatcc agccatgccg cgtgtgtgaa      360
gaaggccttc gggttgtaaa gcactttcag cgaggaagaa cgcctagtgg ttaataccca      420
ttaggaaag                                                              429

<210> SEQ ID NO 3
<211> LENGTH: 24
<212> TYPE: DNA
<213> ORGANISM: Artificial Sequence
<220> FEATURE:
<223> OTHER INFORMATION: Synthetic primer

<400> SEQUENCE: 3
cataagatta gcggatccta cctg                                              24

<210> SEQ ID NO 4
<211> LENGTH: 25
<212> TYPE: DNA
<213> ORGANISM: Artificial Sequence
<220> FEATURE:
<223> OTHER INFORMATION: Synthetic primer

<400> SEQUENCE: 4
cagcttgtcc agcagggttg tccac                                             25

<210> SEQ ID NO 5
<211> LENGTH: 30
<212> TYPE: DNA
<213> ORGANISM: Artificial Sequence
<220> FEATURE:
<223> OTHER INFORMATION: Synthetic primer

<400> SEQUENCE: 5
```
cgaatattga ttacagtcat ccggaagtac                                        30

<210> SEQ ID NO 6
<211> LENGTH: 25
<212> TYPE: DNA
<213> ORGANISM: Artificial Sequence
<220> FEATURE:
<223> OTHER INFORMATION: Synthetic primer

<400> SEQUENCE: 6
ggatgcccgt atgaagaaga tcacc                                             25

<210> SEQ ID NO 7
<211> LENGTH: 28
<212> TYPE: DNA
<213> ORGANISM: Artificial Sequence
<220> FEATURE:
<223> OTHER INFORMATION: Synthetic primer

<400> SEQUENCE: 7
ccacgttcat ccggttccag tgctctcc                                          28

<210> SEQ ID NO 8
<211> LENGTH: 26
<212> TYPE: DNA
<213> ORGANISM: Artificial Sequence
<220> FEATURE:
<223> OTHER INFORMATION: Synthetic primer

<400> SEQUENCE: 8
gatcaaattc cccaagatcg tacagg                                            26

<210> SEQ ID NO 9
<211> LENGTH: 1509
<212> TYPE: DNA
<213> ORGANISM: Halomonas sp.

<400> SEQUENCE: 9
atgaaaaaga cgttgctgac tggaatggcg gtcttcatgc tgatgccgtc gggtacggcg        60
ctggcggaag cggaaaatgg cacgatgatg cagtattttg aatggcacct cgaaaacgac       120
ggagagcact ggaaccggat gaacgtggaa gctgaggcgc tgagtgaagc tggcatcacg       180
gcactctgga ttccgccggc ttacaaagga tccggacagg gggatgtcgg ctacggagcc       240
tacgacctgt acgatcttgg ggaatttgat caaaaaggaa ccgtacggac aaaatacggt       300
acaaaagcag agctggaatc agccatcgat gaagtgcagt cgcaaggcat ccaggtatac       360
ggcgacgttg tcatgaatca aaaatgggga gctgatttta cagaagcagt cgaggcggtg       420
caggtgaacc gttccaaccg gcagcaggac atttccggtg cgtatgaaat tgaagcgtgg       480
accggcttcg actttccggg aagggacggt gtttattccg attttcagtg gcgctggttt       540
cattttaacg gcgtagactg ggatgcccgc tatgaagaag atcaccttt ccggctcgca       600
catacggggt ggaattccga tgtcgacctg gagtacggca actacgatta cctgcttggg       660
tcgaatattg attacagtca tccggaagta cgggaagaaa tgatgaactg ggcagctgg       720
tttacagacg agctgaatct cgacggctac cggctgatg cggtgaagca cgtgcccgcc       780
tggtatatga atgactgggt cggctttcag cgggacgaag cggatcagga tctgttcgtc       840
gtcggtgaat actgggcgga cgacctcggt gcaattgaga gctatctgga gcggatggac       900
tgggacgtct ccatgttcga cgtgccgctg aactataatt tttatgaagc gtcgagaaca       960
ggcggcagct acgatatgcg gaacctgctg aacggctcgc tcgttgaagc gcatccgatg      1020

-continued

```
catgcggtga cgtttgtcga caatcacgac acgcagccgg gagaatcgct ggagtcgtgg    1080
gtggacgact ggttcaagcc gcttgcctac gccgttattc tgacgcgtga aggcggctat    1140
ccgtctgtct tttacgggga ttactacggg attccgaacg acggtatcgg cgccaagcag    1200
gacatgctcg atacgctgct ggaagcaagg caggactatg cctacggcac ccagcatgac    1260
tactttgacc attgggatgt ggtcggctgg acgcgtgaag gaagcagcag ccaccctggt    1320
tccggcatgg cggccattat gtccaacggc cccggcggat cgaagtggat gtacgtcggc    1380
agcgaccggg ccggggaaac gtggagcgat atgacgggta atcacggcgc gtctgtcacg    1440
ataaacggag acggctgggg tgaattccat acggacggcg gatccgtatc gatttatacg    1500
cagcaataa                                                            1509
```

<210> SEQ ID NO 10
<211> LENGTH: 502
<212> TYPE: PRT
<213> ORGANISM: Halomonas sp.

<400> SEQUENCE: 10

```
Met Lys Lys Thr Leu Leu Thr Gly Met Ala Val Phe Met Leu Met Pro
1               5                   10                  15

Ser Gly Thr Ala Leu Ala Glu Ala Glu Asn Gly Thr Met Met Gln Tyr
            20                  25                  30

Phe Glu Trp His Leu Glu Asn Asp Gly Glu His Trp Asn Arg Met Asn
        35                  40                  45

Val Glu Ala Glu Ala Leu Ser Glu Ala Gly Ile Thr Ala Leu Trp Ile
    50                  55                  60

Pro Pro Ala Tyr Lys Gly Ser Gly Gln Gly Asp Val Gly Tyr Gly Ala
65                  70                  75                  80

Tyr Asp Leu Tyr Asp Leu Gly Glu Phe Asp Gln Lys Gly Thr Val Arg
                85                  90                  95

Thr Lys Tyr Gly Thr Lys Ala Glu Leu Glu Ser Ala Ile Asp Glu Val
            100                 105                 110

Gln Ser Gln Gly Ile Gln Val Tyr Gly Asp Val Val Met Asn His Lys
        115                 120                 125

Met Gly Ala Asp Phe Thr Glu Ala Val Glu Ala Val Gln Val Asn Arg
    130                 135                 140

Ser Asn Arg Gln Gln Asp Ile Ser Gly Ala Tyr Glu Ile Glu Ala Trp
145                 150                 155                 160

Thr Gly Phe Asp Phe Pro Gly Arg Asp Gly Val Tyr Ser Asp Phe Gln
                165                 170                 175

Trp Arg Trp Phe His Phe Asn Gly Val Asp Trp Asp Ala Arg Tyr Glu
            180                 185                 190

Glu Asp His Leu Phe Arg Leu Ala His Thr Gly Trp Asn Ser Asp Val
        195                 200                 205

Asp Leu Glu Tyr Gly Asn Tyr Asp Tyr Leu Leu Gly Ser Asn Ile Asp
    210                 215                 220

Tyr Ser His Pro Glu Val Arg Glu Glu Met Met Asn Trp Gly Ser Trp
225                 230                 235                 240

Phe Thr Asp Glu Leu Asn Leu Asp Gly Tyr Arg Leu Asp Ala Val Lys
                245                 250                 255

His Val Pro Ala Trp Tyr Met Asn Asp Trp Val Gly Phe Gln Arg Asp
            260                 265                 270

Glu Ala Asp Gln Asp Leu Phe Val Val Gly Glu Tyr Trp Ala Asp Asp
```

```
                275                 280                 285
Leu Gly Ala Ile Glu Ser Tyr Leu Glu Arg Met Asp Trp Asp Val Ser
        290                 295                 300

Met Phe Asp Val Pro Leu Asn Tyr Asn Phe Tyr Glu Ala Ser Arg Thr
305                 310                 315                 320

Gly Gly Ser Tyr Asp Met Arg Asn Leu Leu Asn Gly Ser Leu Val Glu
                325                 330                 335

Ala His Pro Met His Ala Val Thr Phe Val Asp Asn His Asp Thr Gln
            340                 345                 350

Pro Gly Glu Ser Leu Glu Ser Trp Val Asp Asp Trp Phe Lys Pro Leu
        355                 360                 365

Ala Tyr Ala Val Ile Leu Thr Arg Glu Gly Gly Tyr Pro Ser Val Phe
370                 375                 380

Tyr Gly Asp Tyr Tyr Gly Ile Pro Asn Asp Gly Ile Gly Ala Lys Gln
385                 390                 395                 400

Asp Met Leu Asp Thr Leu Leu Glu Ala Arg Gln Asp Tyr Ala Tyr Gly
                405                 410                 415

Thr Gln His Asp Tyr Phe Asp His Trp Asp Val Val Gly Trp Thr Arg
            420                 425                 430

Glu Gly Ser Ser Ser His Pro Gly Ser Gly Met Ala Ala Ile Met Ser
        435                 440                 445

Asn Gly Pro Gly Gly Ser Lys Trp Met Tyr Val Gly Ser Asp Arg Ala
450                 455                 460

Gly Glu Thr Trp Ser Asp Met Thr Gly Asn His Gly Ala Ser Val Thr
465                 470                 475                 480

Ile Asn Gly Asp Gly Trp Gly Glu Phe His Thr Asp Gly Gly Ser Val
                485                 490                 495

Ser Ile Tyr Thr Gln Gln
        500

<210> SEQ ID NO 11
<211> LENGTH: 22
<212> TYPE: PRT
<213> ORGANISM: Halomonas sp.

<400> SEQUENCE: 11

Met Lys Lys Thr Leu Leu Thr Gly Met Ala Val Phe Met Leu Met Pro
1               5                   10                  15

Ser Gly Thr Ala Leu Ala
            20

<210> SEQ ID NO 12
<211> LENGTH: 480
<212> TYPE: PRT
<213> ORGANISM: Halomonas sp.

<400> SEQUENCE: 12

Glu Ala Glu Asn Gly Thr Met Met Gln Tyr Phe Glu Trp His Leu Glu
1               5                   10                  15

Asn Asp Gly Glu His Trp Asn Arg Met Asn Val Glu Ala Glu Ala Leu
            20                  25                  30

Ser Glu Ala Gly Ile Thr Ala Leu Trp Ile Pro Pro Ala Tyr Lys Gly
        35                  40                  45

Ser Gly Gln Gly Asp Val Gly Tyr Gly Ala Tyr Asp Leu Tyr Asp Leu
    50                  55                  60

Gly Glu Phe Asp Gln Lys Gly Thr Val Arg Thr Lys Tyr Gly Thr Lys
```

```
            65                  70                  75                  80
        Ala Glu Leu Glu Ser Ala Ile Asp Glu Val Gln Ser Gln Gly Ile Gln
                        85                  90                  95
        Val Tyr Gly Asp Val Val Met Asn His Lys Met Gly Ala Asp Phe Thr
                    100                 105                 110
        Glu Ala Val Glu Ala Val Gln Val Asn Arg Ser Asn Arg Gln Gln Asp
                    115                 120                 125
        Ile Ser Gly Ala Tyr Glu Ile Glu Ala Trp Thr Gly Phe Asp Phe Pro
                130                 135                 140
        Gly Arg Asp Gly Val Tyr Ser Asp Phe Gln Trp Arg Trp Phe His Phe
        145                 150                 155                 160
        Asn Gly Val Asp Trp Asp Ala Arg Tyr Glu Glu Asp His Leu Phe Arg
                        165                 170                 175
        Leu Ala His Thr Gly Trp Asn Ser Asp Val Asp Leu Glu Tyr Gly Asn
                        180                 185                 190
        Tyr Asp Tyr Leu Leu Gly Ser Asn Ile Asp Tyr Ser His Pro Glu Val
                    195                 200                 205
        Arg Glu Glu Met Met Asn Trp Gly Ser Trp Phe Thr Asp Glu Leu Asn
                    210                 215                 220
        Leu Asp Gly Tyr Arg Leu Asp Ala Val Lys His Val Pro Ala Trp Tyr
        225                 230                 235                 240
        Met Asn Asp Trp Val Gly Phe Gln Arg Asp Glu Ala Asp Gln Asp Leu
                        245                 250                 255
        Phe Val Val Gly Glu Tyr Trp Ala Asp Asp Leu Gly Ala Ile Glu Ser
                        260                 265                 270
        Tyr Leu Glu Arg Met Asp Trp Asp Val Ser Met Phe Asp Val Pro Leu
                    275                 280                 285
        Asn Tyr Asn Phe Tyr Glu Ala Ser Arg Thr Gly Gly Ser Tyr Asp Met
                    290                 295                 300
        Arg Asn Leu Leu Asn Gly Ser Leu Val Glu Ala His Pro Met His Ala
        305                 310                 315                 320
        Val Thr Phe Val Asp Asn His Asp Thr Gln Pro Gly Glu Ser Leu Glu
                        325                 330                 335
        Ser Trp Val Asp Asp Trp Phe Lys Pro Leu Ala Tyr Ala Val Ile Leu
                        340                 345                 350
        Thr Arg Glu Gly Gly Tyr Pro Ser Val Phe Tyr Gly Asp Tyr Tyr Gly
                    355                 360                 365
        Ile Pro Asn Asp Gly Ile Gly Ala Lys Gln Asp Met Leu Asp Thr Leu
                370                 375                 380
        Leu Glu Ala Arg Gln Asp Tyr Ala Tyr Gly Thr Gln His Asp Tyr Phe
        385                 390                 395                 400
        Asp His Trp Asp Val Val Gly Trp Thr Arg Glu Gly Ser Ser Ser His
                        405                 410                 415
        Pro Gly Ser Gly Met Ala Ala Ile Met Ser Asn Gly Pro Gly Gly Ser
                        420                 425                 430
        Lys Trp Met Tyr Val Gly Ser Asp Arg Ala Gly Glu Thr Trp Ser Asp
                    435                 440                 445
        Met Thr Gly Asn His Gly Ala Ser Val Thr Ile Asn Gly Asp Gly Trp
                450                 455                 460
        Gly Glu Phe His Thr Asp Gly Gly Ser Val Ser Ile Tyr Thr Gln Gln
        465                 470                 475                 480

<210> SEQ ID NO 13
```

```
<211> LENGTH: 43
<212> TYPE: DNA
<213> ORGANISM: Artificial Sequence
<220> FEATURE:
<223> OTHER INFORMATION: Synthetic primer

<400> SEQUENCE: 13
cattctgcag cttcagcaga agcggaaaat ggcacgatga tgc          43

<210> SEQ ID NO 14
<211> LENGTH: 35
<212> TYPE: DNA
<213> ORGANISM: Artificial Sequence
<220> FEATURE:
<223> OTHER INFORMATION: Synthetic primer

<400> SEQUENCE: 14
cctctgttaa cttattgctg cgtataaatc gatac                    35

<210> SEQ ID NO 15
<211> LENGTH: 22
<212> TYPE: DNA
<213> ORGANISM: Artificial Sequence
<220> FEATURE:
<223> OTHER INFORMATION: Synthetic primer

<400> SEQUENCE: 15
tacatatgag ttatgcagtt tg                                  22

<210> SEQ ID NO 16
<211> LENGTH: 22
<212> TYPE: DNA
<213> ORGANISM: Artificial Sequence
<220> FEATURE:
<223> OTHER INFORMATION: Synthetic primer

<400> SEQUENCE: 16
gttatgagtt agttcaaatt cg                                  22

<210> SEQ ID NO 17
<211> LENGTH: 27
<212> TYPE: DNA
<213> ORGANISM: Artificial Sequence
<220> FEATURE:
<223> OTHER INFORMATION: Synthetic primer

<400> SEQUENCE: 17
ctccagatag ctctcaattg caccgag                             27

<210> SEQ ID NO 18
<211> LENGTH: 645
<212> TYPE: DNA
<213> ORGANISM: Bacillus sp.

<400> SEQUENCE: 18
aaaatgggtg ctgatttcac cgaagcggtg gatgcggtgc aggtgaatcc ggataaccgt    60
ctgcaagaca tttcggaagc ttacacgatc gacgcttgga caggctttac atttgaagga   120
cgcaagaacg cctattcgga ttttaactgg cactggtacc attttaacgg cgtagactgg   180
gatgaccggt atggggaaag ccacattttc cgcctggcac ataccggatg gaatcatgaa   240
gtggacacag agaagggaa ttatgattat cttctcggct cgaatatcga tttcagccat   300
cccgaggtgc aggacgagct gaaagactgg ggaagctggt atacagagga attaaacctg   360
gacggttacc ggattgatgc ggctaaacat attccgttct ggtatgctga tgactgggtc   420
```

```
gatcaccagc gtacagaagc cggagcggat cagtttgtcg tcagtgaata ctggatagat    480
gatcttggag cactcgagaa ttatttaaga gaactggact gggacgtctc cgtgtttgac    540
gtgccgctga actacaattt ttatgaggca tcccgcaccg ggggaagcta cgatatgcgg    600
aatctgctgg aagggtcgct tgtagaagca catccacagc atgcg                    645
```

<210> SEQ ID NO 19
<211> LENGTH: 1506
<212> TYPE: DNA
<213> ORGANISM: Bacillus sp.

<400> SEQUENCE: 19

```
atgaagaaac gatatgctgg attgcttgtg ctgagcggat tgcttttgcc aacggcagga    60
gtctctgcga tggagaacgg aacgatgatg cagtattacg agtggcatct ggaaaacgac    120
ggggagcatt ggaaccgaat gaatgagcag gcggatgatt tagcggatgc tggtattacg    180
gcgttatgga tcccccccggc ctataaaggg aacagccagc aagacgtcgg ctatggtgcc    240
tatgacttgt atgatttagg agaatttgac caaaaaggaa cggtgcgcac gaagtacggc    300
acaaagcagg agctgcagaa cgcagtgtct tcactgcagt cggaagggct ggaggtatac    360
ggagatgtcg ttttgaatca caaaatgggt gctgatttca ccgaagcggt ggatgcggtg    420
caggtgaatc cggataaccg tctgcaagac atttcggaag cttacacgat cgacgcttgg    480 acaggctttta catttgaagg acgcaagaac gcctattcgg attttaactg gcactggtac    540
cattttaacg gcgtagactg ggatgaccgg tatggggaaa gccacatttt ccgcctggca    600
cataccggat ggaatcatga agtggacaca gagaagggga attatgatta tcttctcggc    660
tcgaatatcg atttcagcca tcccgaggtg caggacgagc tgaaagactg gggaagctgg    720
tatacagagg aattaaaccct ggacggttac cggattgatg cggctaaaca tattccgttc    780
tggtatgctg atgactgggt cgatcaccag cgtacagaag ccggagcgga tcagtttgtc    840
gtcagtgaat actggataga tgatcttgga cactcgaga attattaag agaactggac    900 tgggacgtct ccgtgtttga cgtgccgctg aactacaatt tttatgaggc atcccgcacc    960 ggggaagct acgatatgcg gaatctgctg aagggtcgc ttgtagaagc acatccacag    1020
catgcggtca cgttcgtgga caatcatgat acgcagccgg agagtcgct ggagtcgtgg    1080 gtagatgact ggttcaaacc acttgcctat gcggtgacgc tgacgagaga aggcggctat    1140
ccaagtgttt tttacgggga ttactacggc attccgaacg acaacatctc tgcgaaaaaa    1200
ccaatgttgg atcagctgct ggaggcacgc acggattatt cttacggcac acagcacgat    1260
tattttgacc actgggatat cgttggttgg acgagagaag gaagcacaga agtgagcggc    1320
tcaggacttg ccacactcat gtccaatggt ccaggcggct ccaagtggat gtatgttgga    1380
gcgcagcacg caggagacac ctggacagac atgctcggaa atcacagtgc gcaggtgaca    1440
attaatcaag acggctgggg agaattctat acagatggcg gagccgtttc tgtgtatgtc    1500
caacag                                                                1506
```

<210> SEQ ID NO 20
<211> LENGTH: 1437
<212> TYPE: DNA
<213> ORGANISM: Bacillus sp.

<400> SEQUENCE: 20

```
atggagaacg gaacgatgat gcagtattac gagtggcatc tggaaaacga cggggagcat    60
```

-continued

```
tggaaccgaa tgaatgagca ggcggatgat ttagcggatg ctggtattac ggcgttatgg      120 atcccccgg cctataaagg aacagccag caagacgtcg gctatggtgc ctatgacttg       180
tatgatttag gagaatttga ccaaaaagga acggtgcgca cgaagtacgg cacaaagcag     240
gagctgcaga acgcagtgtc ttcactgcag tcggaagggc tggaggtata cggagatgtc     300
gttttgaatc acaaaatggg tgctgatttc accgaagcgg tggatgcggt gcaggtgaat     360
ccggataacc gtctgcaaga catttcggaa gcttacacga tcgacgcttg gacaggcttt     420
acatttgaag gacgcaagaa cgcctattcg gattttaact ggcactggta ccattttaac     480
ggcgtagact gggatgaccg gtatggggaa agccacattt tccgcctggc acataccgga     540
tggaatcatg aagtggacac agagaagggg aattatgatt atcttctcgg ctcgaatatc     600
gatttcagcc atcccgaggt gcaggacgag ctgaaagact ggggaagctg gtatacagag     660
gaattaaacc tggacggtta ccggattgat gcggctaaac atattccgtt ctggtatgct     720
gatgactggg tcgatcacca gcgtacagaa gccggagcgg atcagtttgt cgtcagtgaa     780
tactggatag atgatcttgg agcactcgag aattatttaa gagaactgga ctgggacgtc     840
tccgtgtttg acgtgccgct gaactacaat ttttatgagg catcccgcac cggggaagc     900 tacgatatgc ggaatctgct ggaagggtcg cttgtagaag cacatccaca gcatgcggtc     960
acgttcgtgg acaatcatga tacgcagccg ggagagtcgc tggagtcgtg ggtagatgac    1020
tggttcaaac cacttgccta tgcggtgacg ctgacgagaa aaggcggcta tccaagtgtt    1080
ttttacgggg attactacgg cattccgaac gacaacatct ctgcgaaaaa accaatgttg    1140
gatcagctgc tggaggcacg cacggattat tcttacggca cacagcacga ttattttgac    1200
cactgggata tcgttggttg gacgagagaa ggaagcacag aagtgagcgg ctcaggactt    1260
gccacactca tgtccaatgg tccaggcggc tccaagtgga tgtatgttgg agcgcagcac    1320
gcaggagaca cctggacaga catgctcgga aatcacagtg cgcaggtgac aattaatcaa    1380
gacggctggg gagaattcta tacagatggc ggagccgttt ctgtgtatgt ccaacag       1437
```

```
<210> SEQ ID NO 21
<211> LENGTH: 69
<212> TYPE: DNA
<213> ORGANISM: Bacillus sp.

<400> SEQUENCE: 21
atgaagaaac gatatgctgg attgcttgtg ctgagcggat tgcttttgcc aacggcagga     60
gtctctgcg                                                             69

<210> SEQ ID NO 22
<211> LENGTH: 480
<212> TYPE: PRT
<213> ORGANISM: Bacillus sp.

<400> SEQUENCE: 22
```

Glu Ala Glu Asn Gly Thr Met Met Gln Tyr Phe Glu Trp His Leu Glu
1               5                   10                  15

Asn Asp Gly Glu His Trp Asn Arg Met Asn Val Glu Ala Glu Ala Leu
            20                  25                  30

Ser Glu Ala Gly Ile Thr Ala Leu Trp Ile Pro Pro Ala Tyr Lys Gly
        35                  40                  45

Ser Gly Gln Gly Asp Val Gly Tyr Gly Ala Tyr Asp Leu Tyr Asp Leu
    50                  55                  60

Gly Glu Phe Asp Gln Lys Gly Thr Val Arg Thr Lys Tyr Gly Thr Lys

-continued

```
                65                  70                  75                  80
Ala Glu Leu Glu Ser Ala Ile Asp Glu Val Gln Ser Gln Gly Ile Gln
                        85                  90                  95

Val Tyr Gly Asp Val Val Met Asn His Lys Met Gly Ala Asp Phe Thr
            100                 105                 110

Glu Ala Val Glu Ala Val Gln Val Asn Arg Ser Asn Arg Gln Gln Asp
        115                 120                 125

Ile Ser Gly Ala Tyr Glu Ile Glu Ala Trp Thr Gly Phe Asp Phe Pro
    130                 135                 140

Gly Arg Asp Gly Val Tyr Ser Asp Phe Gln Trp Arg Trp Phe His Phe
145                 150                 155                 160

Asn Gly Val Asp Trp Asp Ala Arg Tyr Glu Glu Asp His Leu Phe Arg
                165                 170                 175

Leu Ala His Thr Gly Trp Asn Ser Asp Val Asp Leu Glu Tyr Gly Asn
            180                 185                 190

Tyr Asp Tyr Leu Leu Gly Ser Asn Ile Asp Tyr Ser His Pro Glu Val
        195                 200                 205

Arg Glu Glu Met Met Asn Trp Gly Ser Trp Phe Thr Asp Glu Leu Asn
    210                 215                 220

Leu Asp Gly Tyr Arg Leu Asp Ala Val Lys His Val Pro Ala Trp Tyr
225                 230                 235                 240

Met Asn Asp Trp Val Gly Phe Gln Arg Asp Glu Ala Asp Gln Asp Leu
                245                 250                 255

Phe Val Val Gly Glu Tyr Trp Ala Asp Asp Leu Gly Ala Ile Glu Ser
            260                 265                 270

Tyr Leu Glu Arg Met Asp Trp Asp Val Ser Met Phe Asp Val Pro Leu
        275                 280                 285

Asn Tyr Asn Phe Tyr Glu Ala Ser Arg Thr Gly Gly Ser Tyr Asp Met
    290                 295                 300

Arg Asn Leu Leu Asn Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Asp Asp Trp Phe Lys Pro Leu Ala Tyr Ala Val Ile Leu
            340                 345                 350

Thr Arg Glu Gly Gly Tyr Pro Ser Val Phe Tyr Gly Asp Tyr Tyr Gly
        355                 360                 365

Ile Pro Asn Asp Gly Ile Gly Ala Lys Gln Asp Met Leu Asp Thr Leu
    370                 375                 380

Leu Glu Ala Arg Gln Asp Tyr Ala Tyr Gly Thr Gln His Asp Tyr Phe
385                 390                 395                 400

Asp His Trp Asp Val Val Gly Trp Thr Arg Glu Gly Ser Ser Ser His
                405                 410                 415

Pro Ser Gly Gly Met Ala Ala Ile Met Ser Asn Gly Pro Gly Gly Ser
            420                 425                 430

Lys Trp Met Tyr Val Gly Ser Asp Arg Ala Gly Glu Thr Trp Ser Asp
        435                 440                 445

Met Thr Gly Asn His Gly Ala Ser Val Thr Ile Asn Gly Asp Gly Trp
    450                 455                 460

Gly Glu Phe His Thr Asp Gly Gly Ser Val Ser Ile Tyr Thr Gln Gln
465                 470                 475                 480
```

<210> SEQ ID NO 23

```
<211> LENGTH: 479
<212> TYPE: PRT
<213> ORGANISM: Bacillus sp.

<400> SEQUENCE: 23

Met Glu Asn Gly Thr Met Met Gln Tyr Tyr Glu Trp His Leu Glu Asn
1               5                   10                  15

Asp Gly Glu His Trp Asn Arg Met Asn Glu Gln Ala Asp Asp Leu Ala
            20                  25                  30

Asp Ala Gly Ile Thr Ala Leu Trp Ile Pro Pro Ala Tyr Lys Gly Asn
        35                  40                  45

Ser Gln Gln Asp Val Gly Tyr Gly Ala Tyr Asp Leu Tyr Asp Leu Gly
    50                  55                  60

Glu Phe Asp Gln Lys Gly Thr Val Arg Thr Lys Tyr Gly Thr Lys Gln
65                  70                  75                  80

Glu Leu Gln Asn Ala Val Ser Ser Leu Gln Ser Glu Gly Leu Glu Val
                85                  90                  95

Tyr Gly Asp Val Val Leu Asn His Lys Met Gly Ala Asp Phe Thr Glu
            100                 105                 110

Ala Val Asp Ala Val Gln Val Asn Pro Asp Asn Arg Leu Gln Asp Ile
        115                 120                 125

Ser Glu Ala Tyr Thr Ile Asp Ala Trp Thr Gly Phe Thr Phe Glu Gly
    130                 135                 140

Arg Lys Asn Ala Tyr Ser Asp Phe Asn Trp His Trp Tyr His Phe Asn
145                 150                 155                 160

Gly Val Asp Trp Asp Asp Arg Tyr Gly Glu Ser His Ile Phe Arg Leu
                165                 170                 175

Ala His Thr Gly Trp Asn His Glu Val Asp Thr Glu Lys Gly Asn Tyr
            180                 185                 190

Asp Tyr Leu Leu Gly Ser Asn Ile Asp Phe Ser His Pro Glu Val Gln
        195                 200                 205

Asp Glu Leu Lys Asp Trp Gly Ser Trp Tyr Thr Glu Glu Leu Asn Leu
    210                 215                 220

Asp Gly Tyr Arg Ile Asp Ala Ala Lys His Ile Pro Phe Trp Tyr Ala
225                 230                 235                 240

Asp Asp Trp Val Asp His Gln Arg Thr Glu Ala Gly Ala Asp Gln Phe
                245                 250                 255

Val Val Ser Glu Tyr Trp Ile Asp Asp Leu Gly Ala Leu Glu Asn Tyr
            260                 265                 270

Leu Arg Glu Leu Asp Trp Asp Val Ser Val Phe Asp Val Pro Leu Asn
        275                 280                 285

Tyr Asn Phe Tyr Glu Ala Ser Arg Thr Gly Gly Ser Tyr Asp Met Arg
    290                 295                 300

Asn Leu Leu Glu Gly Ser Leu Val Glu Ala His Pro Gln His Ala Val
305                 310                 315                 320

Thr Phe Val Asp Asn His Asp Thr Gln Pro Gly Glu Ser Leu Glu Ser
                325                 330                 335

Trp Val Asp Asp Trp Phe Lys Pro Leu Ala Tyr Ala Val Thr Leu Thr
            340                 345                 350

Arg Glu Gly Gly Tyr Pro Ser Val Phe Tyr Gly Asp Tyr Tyr Gly Ile
        355                 360                 365

Pro Asn Asp Asn Ile Ser Ala Lys Lys Pro Met Leu Asp Gln Leu Leu
    370                 375                 380

Glu Ala Arg Thr Asp Tyr Ser Tyr Gly Thr Gln His Asp Tyr Phe Asp
```

385                 390                 395                 400
His Trp Asp Ile Val Gly Trp Thr Arg Glu Gly Ser Thr Glu Val Ser
                    405                 410                 415

Gly Ser Gly Leu Ala Thr Leu Met Ser Asn Gly Pro Gly Gly Ser Lys
                420                 425                 430

Trp Met Tyr Val Gly Ala Gln His Ala Gly Asp Thr Trp Thr Asp Met
            435                 440                 445

Leu Gly Asn His Ser Ala Gln Val Thr Ile Asn Gln Asp Gly Trp Gly
        450                 455                 460

Glu Phe Tyr Thr Asp Gly Gly Ala Val Ser Val Tyr Val Gln Gln
465                 470                 475

<210> SEQ ID NO 24
<211> LENGTH: 23
<212> TYPE: PRT
<213> ORGANISM: Bacillus sp.

<400> SEQUENCE: 24

Met Lys Lys Arg Tyr Ala Gly Leu Leu Val Leu Ser Gly Leu Leu Leu
1               5                   10                  15

Pro Thr Ala Gly Val Ser Ala
            20

<210> SEQ ID NO 25
<211> LENGTH: 18
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 25
gaygtngtna tgaaycay                                                  18

<210> SEQ ID NO 26
<211> LENGTH: 23
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 26
tcrtgrttnt cnacraangt nac                                            23

<210> SEQ ID NO 27
<211> LENGTH: 21
<212> TYPE: DNA
<213> ORGANISM: Artificial Sequence
<220> FEATURE:
<223> OTHER INFORMATION: Synthetic primer

<400> SEQUENCE: 27
atgatgcart wyttygartg g                                              21

<210> SEQ ID NO 28
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 28 aantynccccc anccrtcnsc rttngtnac                                     29

<210> SEQ ID NO 29
<211> LENGTH: 29
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (3)..(3)
<223> OTHER INFORMATION: n is inosine
<220> FEATURE:
<221> NAME/KEY: misc_feature
<222> LOCATION: (9)..(9)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (15)..(15)
<223> OTHER INFORMATION: n is inosine
<220> FEATURE:
<221> NAME/KEY: misc_feature
<222> LOCATION: (18)..(18)
<223> OTHER INFORMATION: n is inosine
<220> FEATURE:
<221> NAME/KEY: misc_feature
<222> LOCATION: (21)..(21)
<223> OTHER INFORMATION: n is inosine

```
<220> FEATURE:
<221> NAME/KEY: misc_feature
<222> LOCATION: (24)..(24)
<223> OTHER INFORMATION: n is a, c, g, or t

<400> SEQUENCE: 29
ttnacraana cnswnacnsw nccnccrtt                                            29

<210> SEQ ID NO 30
<211> LENGTH: 34
<212> TYPE: DNA
<213> ORGANISM: Artificial Sequence
<220> FEATURE:
<223> OTHER INFORMATION: Synthetic primer

<400> SEQUENCE: 30
ctaaatcata caagtcatag gcaccatagc cgac                                      34

<210> SEQ ID NO 31
<211> LENGTH: 29
<212> TYPE: DNA
<213> ORGANISM: Artificial Sequence
<220> FEATURE:
<223> OTHER INFORMATION: Synthetic primer

<400> SEQUENCE: 31
gcagctcctg ctttgtgccg tacttcgtg                                            29

<210> SEQ ID NO 32
<211> LENGTH: 29
<212> TYPE: DNA
<213> ORGANISM: Artificial Sequence
<220> FEATURE:
<223> OTHER INFORMATION: Synthetic primer

<400> SEQUENCE: 32
gaccactggg atatcgttgg ttggacgag                                            29

<210> SEQ ID NO 33
<211> LENGTH: 29
<212> TYPE: DNA
<213> ORGANISM: Artificial Sequence
<220> FEATURE:
<223> OTHER INFORMATION: Synthetic primer

<400> SEQUENCE: 33
cacgcacgga ttattcttac ggcacacag                                            29

<210> SEQ ID NO 34
<211> LENGTH: 501
<212> TYPE: PRT
<213> ORGANISM: Bacillus sp.

<400> SEQUENCE: 34

Met Arg Arg Trp Val Val Ala Met Leu Ala Val Leu Phe Leu Phe Pro
1               5                   10                  15

Ser Val Val Ala Asp Gly Leu Asn Gly Thr Met Met Gln Tyr Tyr
            20                  25                  30

Glu Trp His Leu Glu Asn Asp Gly Gln His Trp Asn Arg Leu His Asp
        35                  40                  45

Asp Ala Ala Ala Leu Ser Asp Ala Gly Ile Thr Ala Ile Trp Ile Pro
    50                  55                  60

Pro Ala Tyr Lys Gly Asn Ser Gln Ala Asp Val Gly Tyr Gly Ala Tyr
65                  70                  75                  80
```

-continued

```
Asp Leu Tyr Asp Leu Gly Glu Phe Asn Gln Lys Gly Thr Val Arg Thr
                85                  90                  95
Lys Tyr Gly Thr Lys Ala Gln Leu Glu Arg Ala Ile Gly Ser Leu Lys
            100                 105                 110
Ser Asn Asp Ile Asn Val Tyr Gly Asp Val Val Met Asn His Lys Met
        115                 120                 125
Gly Ala Asp Phe Thr Glu Ala Val Gln Ala Val Gln Val Asn Pro Thr
    130                 135                 140
Asn Arg Trp Gln Asp Ile Ser Gly Ala Tyr Thr Ile Asp Ala Trp Thr
145                 150                 155                 160
Gly Phe Asp Phe Ser Gly Arg Asn Asn Ala Tyr Ser Asp Phe Lys Trp
                165                 170                 175
Arg Trp Phe His Phe Asn Gly Val Asp Trp Asp Gln Arg Tyr Gln Glu
            180                 185                 190
Asn His Ile Phe Arg Phe Ala Asn Thr Asn Trp Asn Trp Arg Val Asp
        195                 200                 205
Glu Glu Asn Gly Asn Tyr Asp Tyr Leu Leu Gly Ser Asn Ile Asp Phe
    210                 215                 220
Ser His Pro Glu Val Gln Asp Glu Leu Lys Asp Trp Gly Ser Trp Phe
225                 230                 235                 240
Thr Asp Glu Leu Asp Leu Asp Gly Tyr Arg Leu Asp Ala Ile Lys His
                245                 250                 255
Ile Pro Phe Trp Tyr Thr Ser Asp Trp Val Arg His Gln Arg Asn Glu
            260                 265                 270
Ala Asp Gln Asp Leu Phe Val Val Gly Glu Tyr Trp Lys Asp Asp Val
        275                 280                 285
Gly Ala Leu Glu Phe Tyr Leu Asp Glu Met Asn Trp Glu Met Ser Leu
    290                 295                 300
Phe Asp Val Pro Leu Asn Tyr Asn Phe Tyr Arg Ala Ser Gln Gln Gly
305                 310                 315                 320
Gly Ser Tyr Asp Met Arg Asn Ile Leu Arg Gly Ser Leu Val Glu Ala
                325                 330                 335
His Pro Met His Ala Val Thr Phe Val Asp Asn His Asp Thr Gln Pro
            340                 345                 350
Gly Glu Ser Leu Glu Ser Trp Val Ala Asp Trp Phe Lys Pro Leu Ala
        355                 360                 365
Tyr Ala Thr Ile Leu Thr Arg Glu Gly Gly Tyr Pro Asn Val Phe Tyr
    370                 375                 380
Gly Asp Tyr Tyr Gly Ile Pro Asn Asp Asn Ile Ser Ala Lys Lys Asp
385                 390                 395                 400
Met Ile Asp Glu Leu Leu Asp Ala Arg Gln Asn Tyr Ala Tyr Gly Thr
                405                 410                 415
Gln His Asp Tyr Phe Asp His Trp Asp Val Val Gly Trp Thr Arg Glu
            420                 425                 430
Gly Ser Ser Ser Arg Pro Asn Ser Gly Leu Ala Thr Ile Met Ser Asn
        435                 440                 445
Gly Pro Gly Gly Ser Lys Trp Met Tyr Val Gly Arg Gln Asn Ala Gly
    450                 455                 460
Gln Thr Trp Thr Asp Leu Thr Gly Asn Asn Gly Ala Ser Val Thr Ile
465                 470                 475                 480
Asn Gly Asp Gly Trp Gly Glu Phe Phe Thr Asn Gly Gly Ser Val Ser
                485                 490                 495
```

Val Tyr Val Asn Gln
            500

<210> SEQ ID NO 35
<211> LENGTH: 480
<212> TYPE: PRT
<213> ORGANISM: Bacillus sp.

<400> SEQUENCE: 35

Asp Gly Leu Asn Gly Thr Met Met Gln Tyr Tyr Glu Trp His Leu Glu
1               5                   10                  15

Asn Asp Gly Gln His Trp Asn Arg Leu His Asp Asp Ala Ala Ala Leu
            20                  25                  30

Ser Asp Ala Gly Ile Thr Ala Ile Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Ala Gln Leu Glu Arg Ala Ile Gly Ser Leu Lys Ser Asn Asp Ile Asn
                85                  90                  95

Val Tyr Gly Asp Val Val Met Asn His Lys Met Gly Ala Asp Phe Thr
            100                 105                 110

Glu Ala Val Gln Ala Val Gln Val Asn Pro Thr Asn Arg Trp Gln Asp
        115                 120                 125

Ile Ser Gly Ala Tyr Thr Ile Asp Ala Trp Thr Gly Phe Asp Phe Ser
    130                 135                 140

Gly Arg Asn Asn Ala Tyr Ser Asp Phe Lys Trp Arg Trp Phe His Phe
145                 150                 155                 160

Asn Gly Val Asp Trp Asp Gln Arg Tyr Gln Glu Asn His Ile Phe Arg
                165                 170                 175

Phe Ala Asn Thr Asn Trp Asn Trp Arg Val Asp Glu Glu Asn Gly Asn
            180                 185                 190

Tyr Asp Tyr Leu Leu Gly Ser Asn Ile Asp Phe Ser His Pro Glu Val
        195                 200                 205

Gln Asp Glu Leu Lys Asp Trp Gly Ser Trp Phe Thr Asp Glu Leu Asp
    210                 215                 220

Leu Asp Gly Tyr Arg Leu Asp Ala Ile Lys His Ile Pro Phe Trp Tyr
225                 230                 235                 240

Thr Ser Asp Trp Val Arg His Gln Arg Asn Glu Ala Asp Gln Asp Leu
                245                 250                 255

Phe Val Val Gly Glu Tyr Trp Lys Asp Asp Val Gly Ala Leu Glu Phe
            260                 265                 270

Tyr Leu Asp Glu Met Asn Trp Glu Met Ser Leu Phe Asp Val Pro Leu
        275                 280                 285

Asn Tyr Asn Phe Tyr Arg Ala Ser Gln Gln Gly Gly Ser Tyr Asp Met
    290                 295                 300

Arg Asn Ile Leu Arg Gly Ser Leu Val Glu Ala His Pro Met His Ala
305                 310                 315                 320

Val Thr Phe Val Asp Asn His Asp Thr Gln Pro Gly Glu Ser Leu Glu
                325                 330                 335

Ser Trp Val Ala Asp Trp Phe Lys Pro Leu Ala Tyr Ala Thr Ile Leu
            340                 345                 350

Thr Arg Glu Gly Gly Tyr Pro Asn Val Phe Tyr Gly Asp Tyr Tyr Gly
        355                 360                 365

Ile Pro Asn Asp Asn Ile Ser Ala Lys Lys Asp Met Ile Asp Glu Leu
    370                 375                 380

Leu Asp Ala Arg Gln Asn Tyr Ala Tyr Gly Thr Gln His Asp Tyr Phe
385                 390                 395                 400

Asp His Trp Asp Val Val Gly Trp Thr Arg Glu Gly Ser Ser Ser Arg
                405                 410                 415

Pro Asn Ser Gly Leu Ala Thr Ile Met Ser Asn Gly Pro Gly Gly Ser
            420                 425                 430

Lys Trp Met Tyr Val Gly Arg Gln Asn Ala Gly Gln Thr Trp Thr Asp
        435                 440                 445

Leu Thr Gly Asn Asn Gly Ala Ser Val Thr Ile Asn Gly Asp Gly Trp
    450                 455                 460

Gly Glu Phe Phe Thr Asn Gly Gly Ser Val Ser Val Tyr Val Asn Gln
465                 470                 475                 480

<210> SEQ ID NO 36
<211> LENGTH: 28
<212> TYPE: DNA
<213> ORGANISM: Artificial Sequence
<220> FEATURE:
<223> OTHER INFORMATION: Synthetic primer

<400> SEQUENCE: 36
tacgccgtta aaatggtacc agtgccag                                    28

<210> SEQ ID NO 37
<211> LENGTH: 29
<212> TYPE: DNA
<213> ORGANISM: Artificial Sequence
<220> FEATURE:
<223> OTHER INFORMATION: Synthetic primer

<400> SEQUENCE: 37
cacgcacgga ttattcttac ggcacacag                                   29

<210> SEQ ID NO 38
<211> LENGTH: 29
<212> TYPE: DNA
<213> ORGANISM: Artificial Sequence
<220> FEATURE:
<223> OTHER INFORMATION: Synthetic primer

<400> SEQUENCE: 38
attcacctgc accgcatcca ccgcttcgg                                   29

<210> SEQ ID NO 39
<211> LENGTH: 29
<212> TYPE: DNA
<213> ORGANISM: Artificial Sequence
<220> FEATURE:
<223> OTHER INFORMATION: Synthetic primer

<400> SEQUENCE: 39
gaccactggg atatcgttgg ttggacgag                                   29

<210> SEQ ID NO 40
<211> LENGTH: 24
<212> TYPE: DNA
<213> ORGANISM: Artificial Sequence
<220> FEATURE:
<223> OTHER INFORMATION: Synthetic primer

<400> SEQUENCE: 40

```
cactttatgc ttccggctcg tatg                                              24
```

<210> SEQ ID NO 41
<211> LENGTH: 23
<212> TYPE: DNA
<213> ORGANISM: Artificial Sequence
<220> FEATURE:
<223> OTHER INFORMATION: Synthetic primer

<400> SEQUENCE: 41

```
tcgccattca ggctgcgcaa ctg                                               23
```

<210> SEQ ID NO 42
<211> LENGTH: 459
<212> TYPE: PRT
<213> ORGANISM: Artificial Sequence
<220> FEATURE:
<223> OTHER INFORMATION: Consensus sequence resulting from alignment of
      amylase sequences derived from Halomonas and Bacillus strains

<400> SEQUENCE: 42

```
Asp Ala Glu Asn Gly Thr Met Met Gln Tyr Tyr Glu Trp His Leu Glu
1               5                   10                  15

Asn Asp Gly Glu His Trp Asn Arg Met Asn Asp Asp Ala Asp Ala Leu
            20                  25                  30

Ser Asp Ala Gly Ile Thr Ala Leu Trp Ile Pro Pro Ala Tyr Lys Gly
        35                  40                  45

Asn Ser Gln Ala Asp Val Gly Tyr Gly Ala Tyr Asp Leu Tyr Asp Leu
    50                  55                  60

Gly Glu Phe Asp Gln Lys Gly Thr Val Arg Thr Lys Tyr Gly Thr Lys
65                  70                  75                  80

Ala Glu Leu Glu Ala Ile Ser Leu Gln Ser Asn Gly Ile Asn Val Tyr
                85                  90                  95

Gly Asp Val Val Met Asn His Lys Met Gly Ala Asp Phe Thr Glu Ala
            100                 105                 110

Val Asp Ala Val Gln Val Asn Pro Ser Asn Arg Gln Asp Ile Ser Gly
        115                 120                 125

Ala Tyr Thr Ile Asp Ala Trp Thr Gly Phe Asp Phe Gly Arg Asn Ala
    130                 135                 140

Tyr Ser Asp Phe Asn Trp Arg Trp Phe His Phe Asn Gly Val Asp Trp
145                 150                 155                 160

Asp Arg Tyr Glu His Ile Phe Arg Leu Ala His Thr Gly Trp Asn Asp
                165                 170                 175

Val Asp Glu Gly Asn Tyr Asp Tyr Leu Leu Gly Ser Asn Ile Asp Phe
            180                 185                 190

Ser His Pro Glu Val Gln Asp Glu Leu Lys Asp Trp Gly Ser Trp Phe
        195                 200                 205

Thr Asp Glu Leu Asn Leu Asp Gly Tyr Arg Leu Asp Ala Ile Lys His
    210                 215                 220

Ile Pro Phe Trp Tyr Asp Trp Val His Gln Arg Glu Ala Asp Gln Asp
225                 230                 235                 240

Leu Phe Val Val Gly Glu Tyr Trp Asp Leu Gly Ala Leu Glu Tyr
                245                 250                 255

Leu Asp Glu Met Asp Trp Asp Val Ser Leu Phe Asp Val Pro Leu Asn
            260                 265                 270

Tyr Asn Phe Tyr Glu Ala Ser Arg Thr Gly Gly Ser Tyr Asp Met Arg
        275                 280                 285
```

```
Asn Leu Leu Gly Ser Leu Val Glu Ala His Pro Met His Ala Val Thr
    290             295             300

Phe Val Asp Asn His Asp Thr Gln Pro Gly Glu Ser Leu Glu Ser Trp
305             310             315             320

Val Asp Asp Trp Phe Lys Pro Leu Ala Tyr Ala Val Ile Leu Thr Arg
                325             330             335

Glu Gly Gly Tyr Pro Ser Val Phe Tyr Gly Asp Tyr Tyr Gly Ile Pro
            340             345             350

Asn Asp Asn Ile Ser Ala Lys Lys Asp Met Leu Asp Leu Leu Glu Ala
        355             360             365

Arg Gln Asp Tyr Ala Tyr Gly Thr Gln His Asp Tyr Phe Asp His Trp
    370             375             380

Asp Val Val Gly Trp Thr Arg Glu Gly Ser Ser Ser Pro Gly Ser Gly
385             390             395             400

Leu Ala Thr Ile Met Ser Asn Gly Pro Gly Gly Ser Lys Trp Met Tyr
                405             410             415

Val Gly Ala Gln Ala Gly Asp Thr Trp Thr Asp Met Thr Gly Asn His
                420             425             430

Gly Ala Ser Val Thr Ile Asn Gly Asp Gly Trp Gly Glu Phe His Thr
        435             440             445

Asp Gly Gly Ser Val Ser Val Tyr Val Gln Gln
    450             455
```

HALOMONAS STRAIN WDG195-RELATED ALPHA-AMYLASES, AND METHODS OF USE, THEREOF

PRIORITY

The present application claims priority under 35 USC §371 to International Application No. PCT/US2010/025368, filed Feb. 25, 2010, which claims the benefit of to U.S. Provisional Patent Application Ser. No. 61/167,612, filed on Apr. 8, 2009, both of which are hereby incorporated by reference in their entirety.

SEQUENCE LISTING

The sequence listing submitted via EFS, in compliance with 37 C.F.R. §1.52(e), is incorporated herein by reference. The sequence listing text file submitted via EFS contains the file "31341US_SequenceListing", created on Mar. 19, 2012, which is 48,605 bytes in size.

TECHNICAL FIELD

Disclosed are compositions and methods relating to α-amylase enzymes obtained from *Halomonas* strain WDG195, and to structurally related amylases.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup.

α-amylases (EC 3.2.1.1) hydrolyze starch, glycogen, and related polysaccharides by cleaving internal α-1,4-glucosidic bonds at random. For a number of years, α-amylase enzymes have been used for a variety of different purposes, including starch liquefaction, textile desizing, starch modification in the paper and pulp industry, and for brewing. These enzymes can also be used to remove starchy stains during dishwashing and laundry washing. Laundry and dish soils vary greatly in composition and therefore also in their ability to be removed and few amylases in the market place can be used for both laundry and dish applications.

*Halomonas* species are Gram-negative, moderately halophilic bacteria that grow optimally in media containing 3-15% NaCl, although most will grow over a very wide range of salinities. Some species are alkaliphilic. The only described amylase from *Halomonas* sp. is from *Halomonas meridiana* DSM5425 (Coronado, M. J. et al. (2000) *FEMS Microbiology Letters* 183:67-71). This α-amylase (i.e., amyH) has been cloned and a deduced amino acid sequence (AmyH) predicted (Coronado, M. J. et al., (2000) *Microbiology* 146:861-868). The nucleotide sequence for the amyH gene (AJ239061) and the predicted amino acid sequence for the AmyH polypeptide (CAB92963) are available in GenBank. The amino acid sequence of AmyH is also set forth in SEQ ID NO: 1. AmyH is predicted to be a polypeptide of 457 amino acids, including a signal sequence of 20 amino acids and a mature polypeptide sequence of 437 amino acids.

While AmyH appears to belong to be a family 13 glycosyl hydrolases, it has low sequence identity with its closest homologues, as shown in the following Table:

| Homolog | Sequence identity |
|---|---|
| α-amylase, catalytic region (*Herpetosiphon aurantiacus* ATCC 23779) | 54% |
| α-amylase (*Stigmatella aurantiaca* DW4/3-1) | 54% |
| Glycosidase (*Pseudoalteromonas tunicata* D2) | 54% |
| α-Amylase from *Pseudoalteromonas haloplanctis* | 52% |

SUMMARY

The present compositions and methods relate to an α-amylase from *Halomonas* strain WDG195 and related α-amylases, which represent a unique family of amylases useful for industrial applications. The amylases are referred to collectively as AmyWDG195-related polypeptides or AmyWDG195-related amylases.

In one aspect, an isolated polypeptide is provided, having at least 80% amino acid sequence identity to AmyWDG195 and including at least one of the following amino acid residues at the indicated amino acid position relative to AmyWDG195, as determined by aligning the amino acid sequence of the polypeptide with the amino acid sequence of AmyWDG195: E at position 3, E at position 20, M at position 25, N at position 26, L at position 40, D at position 68, E at position 82, Q at position 91, G at position 94, L at position 177, H at position 179, G at position 181, N at position 224, L at position 267, D at position 278, D at position 280, V at position 281, E at position 294, R at position 297, T at position 298, L at position 307, D at position 340, V at position 350, S at position 360, L at position 381, E at position 386, D at position 390, G at position 418, M at position 449, H at position 453, D at position 470, and Q at position 479.

In some embodiments, the polypeptide includes at least one of the following amino acid residues at the indicated amino acid position relative to AmyWDG195: E at position 3, E at position 20, M at position 25, N at position 26, D at position 68, E at position 82, Q at position 91, G at position 94, L at position 177, H at position 179, G at position 181, N at position 224, D at position 278, D at position 280, V at position 281, E at position 294, R at position 297, T at position 298, D at position 340, V at position 350, S at position 360, E at position 386, D at position 390, G at position 418, M at position 449, H at position 453, D at position 470, and Q at position 479. As above, the AmyWDG195-related polypeptide may have any subset of these amino acid residues at the indicated positions, or all of these amino acid residues at the indicated positions.

In some embodiments, the polypeptide includes at least one of the following amino acid residues at the indicated amino acid position relative to AmyWDG195: M at position 25, N at position 26, L at position 177, H at position 179, E at position 294, T at position 298, and M at position 449.

In some embodiments, the polypeptide includes at least one of the following combinations of amino acid residues at the indicated amino acid position relative to AmyWDG195: M at position 25 and N at position 26, optionally with E at position 20; Q at position 91 and G at position 94; L at position 177, H at position 179, and G at position 181; D at position 280 and V at position 281, optionally with D at position 278; R at position 297 and T at position 298, optionally with E at position 294; E at position 386 and D at position 390, optionally with L at position 381; and M at position 449 and H at position 453.

In some embodiments, the polypeptide includes at least 30 glutamate residues.

In some embodiments, the polypeptide includes at least one of the following amino acid residues at the indicated amino acid position relative to AmyWDG195: N at position 104, D at position 194, N at position 200, and H at position 235.

In some embodiments, the polypeptide includes at least one of the following amino acid residues at the indicated amino acid position relative to AmyWDG195: Y at position 302, G at position 300, N at position 427, D at position 404, and W at position 403

In some embodiments, the polypeptide includes at least one of the following amino acid residues at the indicated amino acid position relative to AmyWDG195: N at position 289, V at position 324, D at position 325, and S at position 337.

In some embodiments, the polypeptide includes the following amino acid residue at the indicated amino acid position relative to AmyWDG195: L at position 197.

In some embodiments, AmyWDG195 has the amino acid sequence of SEQ ID NO: 12. In some embodiments, the polypeptide has at least 90% amino acid sequence identity to the amino acid sequence of SEQ ID NO: 12. In some embodiments, the polypeptide has at least 95% amino acid sequence identity to the amino acid sequence of SEQ ID NO: 12. In particular embodiments, the polypeptide has the amino acid sequence of SEQ ID NO: 12 (AmyWDG195).

In some embodiments, the polypeptide has the amino acid sequence of SEQ ID NO: 23 (AmySWT282).

In some embodiments, the polypeptide has α-amylase activity. In some embodiments, the activity is independent of calcium.

In another aspect, a cultured cell material comprising one or more of any of the aforementioned polypeptides is provided.

In another aspect, a composition comprising one or more of any of the aforementioned polypeptides is provided. In some embodiments, the composition is a cleaning composition. In some embodiments, the composition is effective for removing starchy stains from laundry, dishes, or textiles.

In another aspect, a method for removing a starchy stain from a surface is provided, comprising incubating the surface in the presence of a aqueous composition comprising an effective amount of a polypeptide of claim 1, allowing the polypeptides to hydrolyse starch components present in the starchy stain to produce smaller starch-derived molecules that dissolve in the aqueous composition, thereby removing the starchy stain from the surface.

In some embodiments, the incubating is in the absence of calcium. In some embodiments, the incubating is in the presence of a calcium chelating agent. In some embodiments, the surface is a textile surface.

In another aspect, a method for expressing a polypeptide having amylase activity is provided, comprising:

constructing an expression vector comprising a polynucleotide encoding a signal sequence linked to a polynucleotide encoding a polypeptide of claim 1;

introducing the expression vector into a host cell, expressing the polypeptides in the presence of at least about 1% NaCl, recovering the polypeptide expressed.

In some embodiments, expressing the polypeptide is performed in the presence of at least about 2% NaCl. In some embodiments, expressing the polypeptide is performed in the presence of at least about 3% NaCl.

In some embodiments, the amount of polypeptide expressed in the presence of 1% NaCl is at least 5-fold the amount expressed in minimal media without added NaCl. In some embodiments, the amount of polypeptide expressed in the presence of 2% NaCl is at least 20-fold the amount expressed in minimal media without added NaCl. In some embodiments, the amount of polypeptide expressed in the presence of 1% NaCl is at least 20-fold the amount expressed in minimal media without added NaCl.

In a further aspect, a vector comprising a polynucleotide sequence encoding an AmyWDG195-related amylase is provided. The AmyWDG195-related amylase coding sequence may be operably linked to a promoter or to other control elements. In yet a further aspect, a host cell comprising a polynucleotide encoding an AmyWDG195-related amylase, or vector comprising such a polynucleotide, is provided. The isolated host cell can be a prokaryote or eukaryote. The isolated host cell can be a bacterium (e.g., *B. subtilis, B. licheniformis, B. lentus, B. brevis, Geobacillus* (formerly *Bacillus*) *stearothermophilus, B. alkalophilus, B. amyloliquefaciens, B. coagulans, B. circulans, B. lautus, B. thuringiensis, Streptomyces lividans, S. murinus*, or *Escherichia coli*).

Another aspect contemplates a detergent additive comprising an AmyWDG195-related amylase, wherein the detergent additive is optionally in the form of a non-dusting granulate, microgranulate, stabilized liquid, gel, or protected enzyme. The polypeptide in the detergent additive can be a truncated polypeptide as described above. The detergent additive can contain about 0.02 mg to about 200 mg of polypeptide per gram of the detergent additive. The detergent additive can further comprise an enzyme selected from the group consisting of a protease, a lipase, a peroxidase, an oxidase, an amylolytic enzyme, a cellulase, a polyesterase, and any combination thereof.

Another aspect contemplates a detergent composition comprising any of the described detergent additives. A detergent composition can optionally comprise one or more of: a surfactant, a bleaching system or bleach, a detergent builder, a polymer, a stabilizing agent, a fabric conditioner, a foam booster, a suds suppressor, an anti-corrosion agent, a dye, a perfume, a soil suspending agent, a tarnish inhibitor, an optical brightener, or a bacteriocide. A detergent composition can comprise or further comprise an additional enzyme, wherein the enzyme is a protease, a lipase, a peroxidase, an oxidase, an amylolytic enzyme, a cellulase, a polyesterase, or any combination thereof.

Another aspect contemplates a manual or automatic dishwashing detergent composition comprising an AmyWDG195-related amylase.

Yet a further aspect contemplates a method of washing dishes comprising applying a manual or automatic dishwashing detergent described herein to a dish or dishes in need thereof. The method of washing the dishes contemplates adding the dishwashing detergent in an amount such that the wash liquor contains a polypeptide described herein in the amount of about 0.01 ppm to about 4 ppm.

Another aspect contemplates a laundry detergent composition comprising a detergent additive described herein. Yet a further aspect contemplates a method of cleaning a textile comprising washing a soiled textile in solution with a detergent composition described herein. The method further contemplates having the polypeptide described herein in an amount in the solution of about 0.01 to about 2 ppm in the solution.

These and other aspects and embodiments of the compositions and methods will be apparent from the present description and drawings.

BRIEF DESCRIPTION OF THE DRAWINGS

FIG. 7 shows and alignment of AmyWDG195, AmySWT282, and Amy K38, emphasizing residues conserved between AmyWDG195 and AmySWT282.

FIG. 8 shows and alignment of AmyWDG195, AmySWT282, and Amy K38, showing conserved residues and a consensus sequence.

FIG. 9 lists the polypeptide and nucleotide sequences referred to in the description.

BRIEF DESCRIPTION OF THE SEQUENCES

Figure 1:
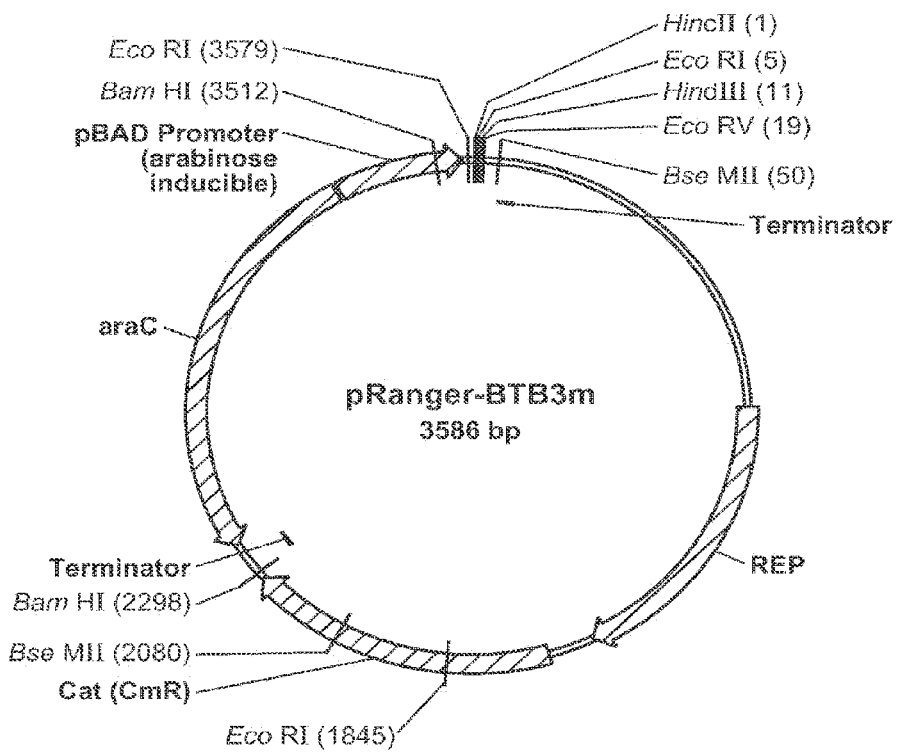
FIG. 1 shows a diagram of the vector pRANGER-BTB3-Cat.

SEQ ID NO: 1 is the amino acid sequence of the AmyH precursor (i.e., immature or full-length) polypeptide from *Halomonas meridiana*, The signal sequence is the first about 20 residues.

SEQ ID NO: 2 is a partial nucleotide sequence of the 16S rRNA gene of *Halomonas* strain WDG195

SEQ ID NOs: 3-8 are the nucleotide sequences of primers described in the Examples.

SEQ ID NO: 9 is the nucleotide sequence of the amyWDG195 gene.

SEQ ID NO: 10 is the amino acid sequence of the AmyWDG195 precursor (i.e., immature or full-length) polypeptide. The signal sequence is the first about 22 residues, with the remaining residue representing the mature polypeptide.

SEQ ID NO: 11 is the amino acid sequence of the AmyWDG195 signal peptide.

SEQ ID NO: 12 is the amino acid sequence of the AmyWDG195 mature polypeptide.

SEQ ID NOs: 13-17 are the nucleotide sequences of primers described in the Examples.

SEQ ID NO: 18 is the partial nucleotide sequence of the AmySWT282 gene.

SEQ ID NO: 19 is the nucleotide sequence encoding the AmySWT282 precursor (i.e., immature or full-length) polypeptide.

SEQ ID NO: 20 is the nucleotide sequence encoding the AmySWT282 mature polypeptide.

SEQ ID NO: 21 is nucleotide sequence encoding the AmySWT282 signal peptide.

SEQ ID NO: 22 is the amino acid sequence of the AmySWT282 precursor (i.e., immature or full-length) polypeptide. The signal sequence is the first about 22 residues, with the remaining residue representing the mature polypeptide.

SEQ ID NO: 23 is the amino acid sequence of the AmySWT282 mature polypeptide.

SEQ ID NO: 24 is the amino acid sequence of the AmySWT282 signal peptide.

SEQ ID NOs: 25-33 are the nucleotide sequences of primers described in the Examples.

SEQ ID NO: 34 is the amino acid sequence of the AmyK38 precursor (i.e., immature or full-length) polypeptide (gi16874476). The signal sequence is the first about 21 residues, with the remaining residue representing the mature polypeptide SEQ ID NO: 35 is the amino acid sequence of the AmyK38 mature polypeptide.

SEQ ID NOs: 36-41 are the nucleotide sequences of primers described in the Examples.

DETAILED DESCRIPTION

Described are compositions and methods relating to an α-amylase isolated from *Halomonas* strain WDG195, herein called "AmyWDG195" (SEQ ID NO: 12). While this amylase belongs to the α-amylase super-family, it is unrelated to AmyH (SEQ ID NO: 1), the amylase previously isolated from *Halomonas meridiana* strain DSM5425, which is assigned to the family 13 glycosyl hydrolases. In particular, AmyWDG195 and AmyH share less than 11% sequence identity.

AmyWDG195 shares significant sequence identity with another heretofore unknown amylase from *Bacillus* sp. strain SWT282, herein called "AmySWT282" (SEQ ID NO: 23), and to a known amylase from *Bacillus* sp. strain K38, herein called "AmyK38" (SEQ ID NO: 35; GenBank accession number BAB71820; Hagihara, H. et al. (2001) *Appl. Environ. Microbiol.* 67:1744-50). In particular, AmyWDG195 shares about 78.1% sequence identity with AmySWT282 and 81.5% sequence identity with AmyK38. Notably, AmySWT282 and AmyK38 share 77.9% sequence identity; therefore, these three amylases are approximately equidistant in evolutionary distance. However, a more refined structural analysis reveals that while AmyWDG195, AmySWT282, AmyK38, share some common features, AmyWDG195 and AmySWT282 are readily distinguishable from AmyK38 based on other features.

In particular, both AmyWDG195 and AmySWT282 include key residues that are associated with binding to three sodium ions in AmyK38 (Hagihari, H. et al. (2001) *Eur. J. Biochem.* 268:3974-82; Nonaka, T. et al. (2003) *J. Biol. Chem.* 278:24818-25). In particular, the presence of N at position 104, D at position 194, N at position 200, and H at position 235, which is associated with the binding of AmyK38 to a first sodium, is conserved in both AmyWDG195 and AmySWT282. Similarly, the presence of Y at position 302, G at position 300, N at position 427, D at position 404, and W at position 403, which is associated with the binding of AmyK38 to a second sodium, and the presence of N at position 289, V at position 324, D at position 325, and S at position 337, which is associated with the binding of AmyK38 to a third sodium, is conserved in both AmyWDG195 and AmySWT282. Accordingly, AmyWDG195 and AmySWT282 are expected to share certain halophilic properties with AmyK38, which is confirmed by experiments described herein. In addition, AmyWDG195, AmySWT282, and AmyK38 all share an L at position 197, unlike many other *Bacillus* amylases which have an M at this position. This makes these amylases less susceptible to chemical oxidation than other *Bacillus* amylases.

In contrast, AmyWDG195 and AmySWT282 can readily be distinguished from AmyK38 based on amino acid residues present at each of 32 different positions, at which AmyWDG195 and AmySWT282 share the same amino acid residue, which is different from that present in AmyK38. AmyWDG195 and AmySWT282 also contain a significantly larger number of glutamate residues and have lower predicted isoelectric points (pI) than AmyK38. Thus, AmyWDG195 and AmySWT282, represent related, heretofore unknown, calcium-independent amylases, which are resistant to chelating reagents and chemical oxidants, making them very attractive for cleaning applications.

For the purposes of the present description, AmyWDG195, AmySWT282, and related polypeptides are referred to collectively as AmyWDG195-related polypeptides or AmyWDG195-related amylases. For convenience, the amino acid position numbering of AmyWDG195 and AmyK38 is used with reference to these polypeptides (see, e.g., FIGS. 7 and 8). However, AmySWT28 is one amino acid shorter at the N-terminus than AmyWDG195 and AmyK38, thereof the actual amino acid positions of AmySWT28 are one less (i.e., −1) with respect to AmyWDG195 and AmyK38.

Various compositions and methods that involve AmyWDG195-related amylase polypeptides, or polynucleotides encoding these polypeptides, are now to be described.

1. Definitions and Acronyms

In accordance with this detailed description, the following abbreviations and definitions apply. Note that the singular forms "a," "an," and "the" include plural referents unless the context clearly dictates otherwise. Thus, for example, reference to "an enzyme" includes a plurality of such enzymes, and reference to "the dosage" includes reference to one or more dosages and equivalents thereof known to those skilled in the art, and so forth.

Unless defined otherwise, all technical and scientific terms used herein have the same meaning as commonly understood by one of ordinary skill in the art. The following abbreviations and/or terms are defined for clarity:

1.1 Abbreviations/Acronyms

The following abbreviations/acronyms have the following meanings unless otherwise specified:
AE alcohol ethoxylate
AEO alcohol ethoxylate
AEOS alcohol ethoxysulfate
AES alcohol ethoxysulfate
AmyWDG195 α-amylase from *Halomonas* strain WDG195
AmyH α-amylase from *Halomonas meridiana* strain DSM5425
AmySWT282 α-amylase from *Bacillus* sp. strain SWT282
AmyK38 α-amylase from *Bacillus* sp. strain K38
AOS α-olefinsulfonate
AS alkyl sulfate
CBD-25 carbohydrate binding domain protein family 25
cDNA complementary DNA
CMC carboxymethylcellulose
DNA deoxyribonucleic acid
DTMPA diethylenetriaminepentaacetic acid
EC enzyme commission
EDTA ethylenediaminetetraacetic acid
EMPA Eidgenössische Materialprüfungs- und Forschungs Anstalt (Swiss Federal Laboratories for Materials Testing and Research)
EO ethylene oxide (polymer fragment)
F&HC fabric & household care
GA glucoamylase
IPTG isopropyl β-D-thiogalactoside
kDa kiloDalton
LAS linear alkylbenzenesulfonate
LAT pertaining to *B. licheniformis* amylase
MW molecular weight
MWU modified Wohlgemuth unit; $1.6 \times 10^{-5}$ mg/MWU=unit of activity
NOBS nonanoyloxybenzenesulfonate
NTA nitriloacetic acid
OxAm Purastar HPAM 5000L (Genencor International, Inc.)
PEG polyethyleneglycol
pI isoelectric point
PVA poly(vinyl alcohol)
PVP poly(vinylpyrrolidone)
RNA ribonucleic acid
SAS alkanesulfonate
SDS-PAGE sodium dodecyl sulfate polyacrylamide gel electrophoresis
sp. species
TAED tetraacetylethylenediamine
w/v weight/volume
w/w weight/weight
v/v volume/volume
wt % weight percent
° C. degrees Centigrade
$H_2O$ water
$dH_2O$ or DI deionized water
$dIH_2O$ deionized water, Milli-Q filtration
g or gm gram
μg microgram
mg milligram
kg kilogram
μL and μl microliter
mL and ml milliliter
mm millimeter
μm micrometer
M molar
mM millimolar
μM micromolar
U unit
sec and " second
min and ' minute
hr hour
DO dissolved oxygen
Genencor Danisco US Inc, Genencor Division, Palo Alto, Calif.
Ncm Newton centimeter
ETOH ethanol
eq. equivalent
N normal
ds or DS dry solids content 1.2 Definitions The terms "amylase" or "amylolytic enzyme" refer to an enzyme that is, among other things, capable of catalyzing the degradation of starch. Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from starch.

As used herein the term "starch" refers to any material comprised of the complex polysaccharide carbohydrates of plants, comprised of amylose and amylopectin with the formula $(C_6H_{10}O_5)_x$, wherein X can be any number. The term includes plant-based materials such as grains, grasses, tubers and roots, and more specifically materials obtained from wheat, barley, corn, rye, rice, sorghum, brans, cassaya, millet, potato, sweet potato, and tapioca.

The terms, "wild-type," "parental," or "reference," with respect to a polypeptide, refer to a naturally-occurring polypeptide that does not include a man-made substitution, insertion, or deletion at one or more amino acid positions. Similarly, the terms "wild-type," "parental," or "reference," with respect to a polynucleotide, refer to a naturally-occurring polynucleotide that does not include a man-made nucleoside change. However, note that a polynucleotide encoding a wild-type, parental, or reference polypeptide is not limited to a naturally-occurring polynucleotide, and encompasses any polynucleotide encoding the wild-type, parental, or reference polypeptide.

The term "variant," with respect to a polypeptide, refers to a polypeptide that differs from a specified wild-type, parental, or reference polypeptide in that it includes a man-made substitution, insertion, or deletion at one or more amino acid positions. Similarly, a the term "variant," with respect to a polynucleotide, refers to a polynucleotide that differs in nucleotide sequence from a specified wild-type, parental, or reference polynucleotide. The identity of the wild-type, parental, or reference polypeptide or polynucleotide will be apparent from context.

The term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell, or express native genes at different levels or under different conditions than found in nature.

The terms "recovered," "isolated," and "separated," refer to a compound, protein (polypeptides), cell, nucleic acid, amino acid, or other specified material or component that is removed from at least one other material or component with which it is naturally associated as found in nature.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

The terms "thermostable" and "thermostability," with reference to an enzyme, refer to the ability of the enzyme to retain activity after exposure to an elevated temperature. The thermostability of an enzyme, such as an amylase enzyme, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range," with reference to an enzyme, refers to the range of pH values under which the enzyme exhibits catalytic activity.

As used herein, the terms "pH stable" and "pH stability," with reference to an enzyme, relate to the ability of the enzyme to retain activity over a wide range of pH values for a predetermined period of time (e.g., 15 min., 30 min, 1 hour).

As used herein, the term "amino acid sequence" is synonymous with the terms "polypeptide," "protein," and "peptide," and are used interchangeably. Where such amino acid sequences exhibit activity, they may be referred to as an "enzyme." The conventional one-letter or three-letter codes for amino acid residues are used, with amino acid sequences being presented in the standard amino-to-carboxy terminal orientation (i.e., N→C).

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acid sequences are presented in a 5'-to-3' orientation.

By "homologue" shall mean an entity having a specified degree of identity with the subject amino acid sequences and the subject nucleotide sequences. A homologous sequence is taken to include an amino acid sequence that is at least 75%, 80%, 85%, 86%, 87%, 88%, 89%, 90%, 91%, 92%, 93%, 94%, 95%, 96%, 97%, 98% or even 99% identical to the subject sequence, using conventional sequence alignment tools (e.g., Clustal, BLAST, and the like). Typically, homologues will include the same active site residues as the subject amino acid sequence, unless otherwise specified.

As used herein, "hybridization" refers to the process by which one strand of nucleic acid base pairs with a complementary strand, as occurs during blot hybridization techniques and PCR techniques. Stringent hybridization conditions are exemplified by the following: 50° C. and 0.2×SSC (1×SSC=0.15 M NaCl, 0.015 M $Na_3$ citrate, pH 7.0). Highly stringent conditions are exemplified by the following: 65° C. and 0.1×SSC (1×SSC=0.15 M NaCl, 0.015 M $Na_3$ citrate, pH 7.0)].

As used herein, a "synthetic" molecule is produced by in vitro chemical or enzymatic synthesis rather than by an organism.

As used herein, the terms "transformed," "stably transformed," and "transgenic," used with reference to a cell means that the cell contains a non-native (e.g., heterologous) nucleic acid sequence integrated into its genome or carried as an episome that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct, including a polynucleotide encoding a polypeptide of interest (e.g., an AmyWDG195-related polypeptide) has been introduced. Exemplary host strains are bacterial cells. The term "host cell" includes protoplasts created from cells, such as those of a *Bacillus* sp.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on a nucleic acid sequence. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or chloramphenicol) and/or genes that confer a metabolic advantage, such as a nutritional advantage on the host cell.

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which coding sequence is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

A "signal sequence" is a sequence of amino acids attached to the N-terminal portion of a protein, which facilitates the secretion of the protein outside the cell. The mature form of an extracellular protein lacks the signal sequence, which is cleaved off during the secretion process.

As used herein, "biologically active" refer to a sequence having a specified biological activity, such an enzymatic activity.

"Water hardness" is a measure of the minerals (e.g., calcium and magnesium) present in water.

As used herein, "a cultured cell material comprising an AmyWDG195-related amylase," or similar language, refers to a cell lysate or supernatant that includes an AmyWDG195-related amylase as a component. The cell material is preferably from a heterologous host that is grown in culture for the purpose of producing the AmyWDG195-related amylase.

All reference cited, herein, are hereby incorporated by reference in their entirety.

2. AmyWDG195-Related Amylase Nucleic Acids and Polypeptides

One aspect of the present compositions and methods is an AmyWDG195-related polypeptide. The polypeptide may correspond to AmyWDG195, AmySWT282, an amylase having a specified degree of identity to AmyWDG195 or AmySWT282, variants of AmyWDG195 or AmySWT282 that include man-made substitutions, insertions, or deletions, or chimeras, thereof. Exemplary AmyWDG195 and AmySWT282 polypeptides have the amino acid sequences of SEQ ID NO: 12 and SEQ ID NO: 23, respectively. Additional polypeptides have at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or even 99% homology/identity to an AmyWDG195 or AmySWT282 polypeptide, such as the polypeptides of SEQ ID NO: 12 and SEQ ID NO: 23. The present compositions and methods exclude an Amy K38 polypeptide, such as a polypeptide having the amino acid sequence of SEQ ID NO: 35.

As noted above, AmyWDG195 and AmySWT282 can be distinguished from AmyK38 based on the amino acid residue that is present at each of 32 different positions, at which AmyWDG195 and AmySWT282 share the same amino acid residue, which is different from that present in AmyK38. Positions occupied by the same amino acid residues in AmyWDG195 and AmySWT282 (using AmyWDG195 numbering) but different in Amy K38 are summarized in the following Table:

| Common positions in AmyWDG195 and AmySWT282 | Equivalent positions in AmyK38 |
|---|---|
| Glu3 | Leu3 |
| Glu20 | Gln20 |
| Met25 | Leu25 |
| Asn26 | His26 |
| Leu40 | Ile40 |
| Asp68 | Asn68 |
| Glu82 | Gln82 |
| Gln91 | Lys91 |
| Gly94 | Asp94 |
| Leu177 | Phe177 |
| His179 | Asn179 |
| Gly182 | Asn182 |
| Asn225 | Asp225 |
| Leu267 | Val267 |
| Asp278 | Asn278 |
| Asp280 | Glu280 |
| Val281 | Met281 |
| Glu294 | Arg294 |
| Arg297 | Gln297 |
| Thr298 | Gln298 |
| Leu307 | Ile307 |
| Asp340 | Ala340 |
| Val350 | Thr350 |
| Ser360 | Asn360 |
| Leu381 | Ile381 |
| Glu386 | Asp386 |
| Asp390 | Asn390 |
| Gly418 | Asn418 |
| Met449 | Leu449 |
| His453 | Asn453 |
| Asp470 | Asn470 |
| Gln479 | Asn479 |

Referring to the above Table and the alignment shown in FIG. 7, in some embodiments, the AmyWDG195-related polypeptide has one of more of the following amino acid residues at the indicated positions: E at position 3, E at position 20, M at position 25, N at position 26, L at position 40, D at position 68, E at position 82, Q at position 91, G at position 94, L at position 177, H at position 179, G at position 181, N at position 224, L at position 267, D at position 278, D at position 280, V at position 281, E at position 294, R at position 297, T at position 298, L at position 307, D at position 340, V at position 350, S at position 360, L at position 381, E at position 386, D at position 390, G at position 418, M at position 449, H at position 453, D at position 470, and Q at position 479. The AmyWDG195-related polypeptide may have any subset of these amino acid residues at the indicated positions, or all of these amino acid residues at the indicated positions.

In some embodiments, the AmyWDG195-related polypeptide has one of more of the following amino acid residues: E at position 3, E at position 20, M at position 25, N at position 26, D at position 68, E at position 82, Q at position 91, G at position 94, L at position 177, H at position 179, G at position 181, N at position 224, D at position 278, D at position 280, V at position 281, E at position 294, R at position 297, T at position 298, D at position 340, V at position 350, S at position 360, E at position 386, D at position 390, G at position 418, M at position 449, H at position 453, D at position 470, and Q at position 479. As above, the AmyWDG195-related polypeptide may have any subset of these amino acid residues at the indicated positions, or all of these amino acid residues at the indicated positions.

In some embodiments, the AmyWDG195-related polypeptide has one of more of the following amino acid residues: M at position 25, N at position 26, L at position 177, H at position 179, E at position 294, T at position 298, and M at position 449. Again, the AmyWDG195-related polypeptide may have any subset of these amino acid residues at the indicated positions, or all of these amino acid residues at the indicated positions.

In some embodiments, the AmyWDG195-related polypeptide has one of more of the following combinations of amino acid residues at the indicated positions: M at position 25 and N at position 26, optionally with E at position 20; Q at position 91 and G at position 94; L at position 177, H at position 179, and G at position 181; D at position 280 and V at position 281, optionally with D at position 278; R at position 297 and T at position 298, optionally with E at position 294; E at position 386 and D at position 390, optionally with L at position 381; and M at position 449 and H at position 453. The AmyWDG195-related polypeptide may have any subset of these amino acid residue combination, or all of these amino acid residue combinations.

In some embodiments, the AmyWDG195-related polypeptide retains N at position 104, D at position 194, N at position 200, and/or H at position 235, which is believed to be associated with binding to a first sodium, Y at position 302, G at position 300, N at position 427, D at position 404, and/or W at position 403, which is believed to be associated with binding to a second sodium, and/or N at position 289, V at position 324, D at position 325, and S at position 337, which is believed to be associated with binding to a third sodium. In some embodiments, the AmyWDG195-related polypeptide retains L at position 197, believed to associated with reduced susceptibility to chemical oxidation.

Also as noted above, AmyWDG195 and AmySWT282 contain a significantly larger number of glutamate residues and have lower predicted isoelectric points (Pi) than AmyK38. These differences are summarized in the following Table:

| Amylase | Number of glutamates | pI |
|---|---|---|
| AmyWDG195 | 36 | 4.42 |
| AmySWT282 | 33 | 4.47 |
| AmyK38 | 23 | 4.73 |

Thus, in some embodiments, the AmyWDG195-related polypeptide has at least 25, at least 26, at least 27, at least 28, at least 29, at least 30, at least 31, at least 32, at least 33, at least 34, at least 35, or even at least 36 glutamate residues. In some embodiments, the AmyWDG195-related polypeptide has a pI of less than 4.7, less than 4.6, or even less than 4.5.

Where the AmyWDG195-related polypeptide is a variant having a specified degree of homology to AmyWDG195 or AmySWT282, one or more of the specified amino acid positions (or combinations, thereof) may be fixed, such that they do not change (i.e., are conserved or retained) in the variant, while the remaining residues are subject to variation. Alternatively or additionally, the number of glutamate residues in the polypeptide is maintained.

The polypeptides may be a "full-length" AmyWDG195-related amylase, which includes a signal sequence, or the mature form of an AmyWDG195-related amylase, which lacks the signal sequence. Exemplary immature forms of the AmyWDG195 and AmySWT282 polypeptides have the amino acid sequences of SEQ ID NO: 10 and SEQ ID NO: 22, respectively, while exemplary mature forms of the AmyWDG195 and AmySWT282 polypeptides have the amino acid sequences of SEQ ID NO: 12 and SEQ ID NO: 23, respectively. Mature forms of the polypeptides are most useful for use in cleaning compositions. The polypeptides may also be a truncated form of an AmyWDG195-related amylase, which lacks the N or C-terminus of the mature form, or fragments of an AmyWDG195-related amylase that retain at least a portion of the α-amylase activity characteristic of the parental AmyWDG195-related amylase.

As noted above, the polypeptides include variant polypeptides, such as those that include man-made substitutions. Exemplary substitutions are conservative amino acid substitutions, such as those listed in the following table.

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Preferred polypeptides retain α-amylase activity but may have altered biochemical properties with reference to a naturally-occurring parental polypeptide. In some cases, the parental polypeptide is that of SEQ ID NOs: 12 or 23.

The polypeptide may also be a chimeric polypeptide that includes at least a portion of an AmyWDG195-related amylase as described, and at least a portion of a second polypeptide. The second polypeptide may be, for example, a second amylase, a heterologous signal sequence, an epitope to allow tracking or purification, or the like. Exemplary heterologous signal sequences are from *B. subtilis* amylase (AmyE) or AprE, and *Streptomyces* CelA.

Another aspect of the present compositions and methods is a nucleic acid encoding an AmyWDG195-related polypeptide. The nucleic acid may encode AmyWDG195, AmySWT282, an amylase having a specified degree of identity to AmyWDG195 or AmySWT282, variants of AmyWDG195 or AmySWT282 that include man-made substitutions, insertions, or deletions, or chimeras, thereof. In one example, the nucleic acid encodes an amylase having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or even 99% homology/identity to an AmyWDG195 or AmySWT282 polypeptide, such as the polypeptides of SEQ ID NO: 12 and SEQ ID NO: 20, respectively. Due to the degeneracy of the genetic code, it is understood that a plurality of nucleic acids may encode the same polypeptide.

The nucleic acid may also have a specified degree of homology to an exemplary polynucleotide encoding an AmyWDG195-related amylase, such as SEQ ID NO: 9, which encodes AmyWDG195 or SEQ ID NO: 20, which encodes AmySWT282. In one example, the nucleic acid has at least 75%, 80%, 85%, 86%, 87%, 88%, 89%, 90%, 91%, 92%, 93%, 94%, 95%, 96%, 97%, 98% or even 99% identity to one or both of these exemplary sequences. In another example, the nucleic acid hybridizes under stringent or very stringent conditions to one of these exemplary sequences.

Nucleic acids may encode a "full-length" or "fl" AmyWDG195-related amylase, which includes a signal sequence, only the mature form of an AmyWDG195-related amylase, which lacks the signal sequence, a truncated form of AmyWDG195-related amylase, which lacks the N or C-terminus of the mature form, or fragments, thereof that retain at least a portion of the α-amylase activity characteristic of the AmyWDG195-related amylase.

A nucleic acid that encodes an AmyWDG195-related amylase can be operably linked to various promoters and regulators in a vector for expression in various host cells. A nucleic acid that encodes an AmyWDG195-related amylase can also be linked to other coding sequences, e.g., to encode a chimeric polypeptide. Exemplary promoters are the *B. subtilis* Amy E and AprE promoters, and the *Streptomyces* CelA promoters.

3. Method of Producing and Purifying Proteins

Methods of producing and purifying proteins that are secreted in to the culture medium from *Bacillus* are known in the art, as are suitable host cells for producing α-amylases. Exemplary methods for producing the α-amylases are disclosed below.

3.1 Materials and Methods for Producing α-Amylases

An AmyWDG195-related amylase can be expressed, in enzyme form, using an expression vector which typically includes control sequences encoding a suitable promoter, operator, ribosome binding site, translation initiation signal, and, optionally, a repressor gene or various activator genes. A large number of vectors are commercially available for use with recombinant DNA procedures, and the choice of vector will often depend on the host cell into which it is to be introduced. The vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into an isolated host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation through dose effect of an essential metabolic pathway gene.

In the vector, the DNA sequence should be operably linked to a suitable promoter sequence. The promoter may be any DNA sequence that shows transcriptional activity in the host cell of choice and may be derived from genes encoding proteins either homologous or heterologous to the host cell. Exemplary promoters for directing the transcription of the DNA sequence encoding an AmyWDG195-related amylase, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the Geobacillus (formerly *Bacillus*) stearothermophilus maltogenic amylase gene (amyM), the promoters of the *Bacillus amyloliquefaciens* α-amylase (amyQ), the promoters of the *Bacillus subtilis* xy1A and xy1B genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When a gene encoding an AmyWDG195-related amylase polypeptide is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. For expression in *Trichoderma reesei*, the CBHII (cellobiohydrolase II) promoter may be used.

An expression vector may also comprise a suitable transcription terminator and, in eukaryotes, polyadenylation sequences operably linked to the DNA sequence encoding an AmyWDG195-related amylase. Termination and polyadenylation sequences may suitably be derived from the same sources as the promoter.

The vector may further comprise a DNA sequence enabling the vector to replicate in the host cell. Examples of such sequences are the origins of replication of plasmids pUC19, pACYC177, pUB110, pE194, pAMB1, and pIJ702.

The vector may also comprise a selectable marker, e.g., a gene the product of which complements a defect in the isolated host cell, such as the dal genes from *B. subtilis* or *B. licheniformis*, or a gene that confers antibiotic resistance such as, e.g., ampicillin, kanamycin, chloramphenicol or tetracycline resistance. Furthermore, the vector may comprise *Aspergillus* selection markers such as amdS, argB, niaD and xxsC, a marker giving rise to hygromycin resistance, or the selection may be accomplished by co-transformation, such as known in the art. See e.g., International PCT Application WO 91/17243.

While intracellular expression or solid-state fermentation may be advantageous in some respects, e.g., when using certain bacteria or fungi as host cells, one aspect contemplates expression of an AmyWDG195-related amylase into the culture medium. In general, the α-amylase comprises a signal sequence at the amino terminus that permits secretion into the culture medium. If desirable, this signal peptide may be replaced by a different sequence, conveniently accomplished by substitution of the DNA sequences encoding the respective signal polypeptide.

Figure 3:
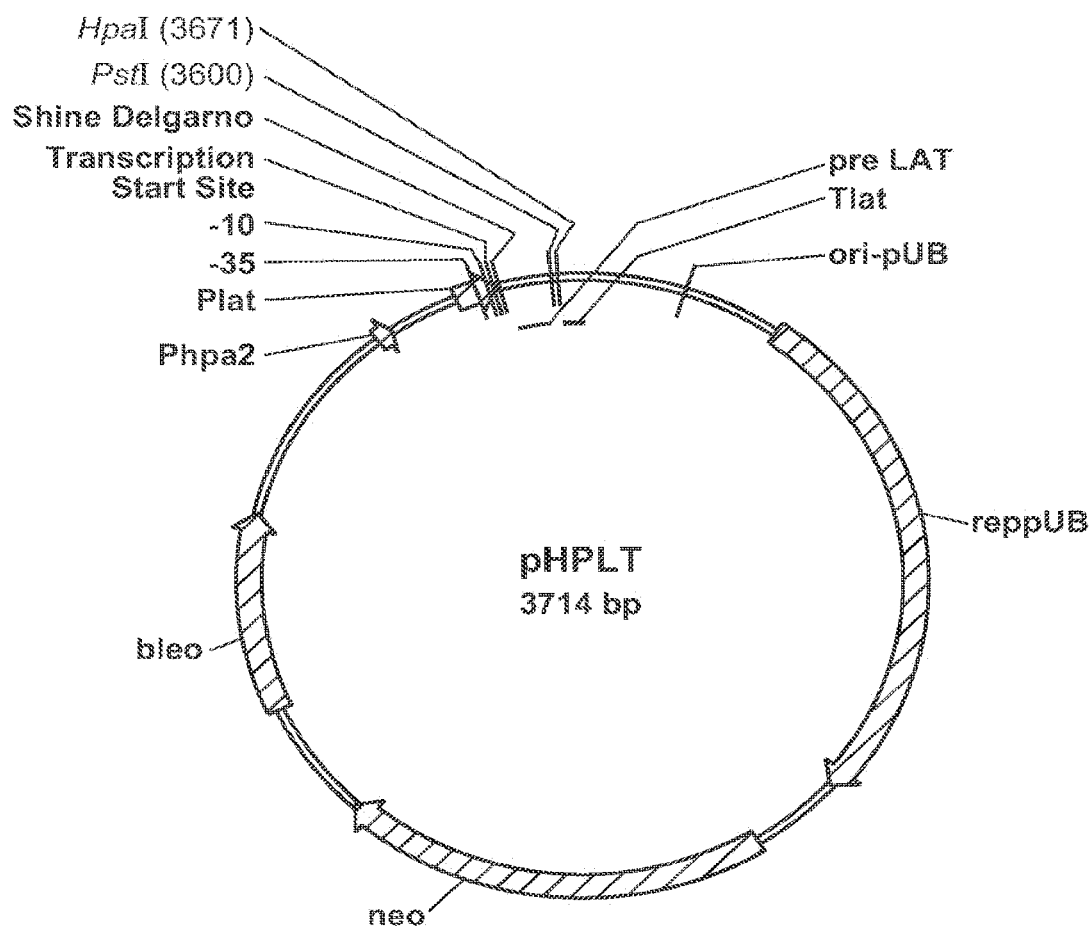
FIG. 3 shows a diagram of the expression vector pHPLT.

The expression vector typically includes the components of a cloning vector, such as, for example, an element that permits autonomous replication of the vector in the selected host organism and one or more phenotypically detectable markers for selection purposes. The expression vector normally comprises control nucleotide sequences such as a promoter, operator, ribosome binding site, translation initiation signal and optionally, a repressor gene or one or more activator genes. Additionally, the expression vector may comprise a sequence coding for an amino acid sequence capable of targeting the AmyWDG195-related polypeptide to a host cell organelle such as a peroxisome, or to a particular host cell compartment. Such a targeting sequence includes but is not limited to the sequence, SKL. For expression under the direction of control sequences, the nucleic acid sequence of the AmyWDG195-related polypeptide is operably linked to the control sequences in proper manner with respect to expression. A portion of an exemplary vector is depicted in FIG. 3.

The procedures used to ligate the DNA construct encoding an AmyWDG195-related polypeptide, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, 2$^{nd}$ ed., Cold Spring Harbor, 1989, and 3$^{rd}$ ed., 2001).

An isolated cell, either comprising a DNA construct or an expression vector, is advantageously used as a host cell in the recombinant production of an AmyWDG195-related amylase. The cell may be transformed with the DNA construct encoding the enzyme, conveniently by integrating the DNA construct (in one or more copies) in the host chromosome. This integration is generally considered to be an advantage, as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Geobacillus* (formerly *Bacillus*) *stearothermophilus, Bacillus alkalophilus, Bacillus amyloliquefaciens, Bacillus coagulans, Bacillus lautus, Bacillus megaterium*, and *Bacillus thuringiensis; Streptomyces* species such as *Streptomyces murinus*; lactic acid bacterial species including *Lactococcus* spp. such as *Lactococcus lactis; Lactobacillus* spp. including *Lactobacillus reuteri; Leuconostoc* spp.; *Pediococcus* spp.; and *Streptococcus* spp. Alternatively, strains of a Gram negative bacterial species belonging to Enterobacteriaceae including *E. coli*, or to Pseudomonadaceae can be selected as the host organism.

A suitable yeast host organism can be selected from the biotechnologically relevant yeasts species such as but not limited to yeast species such as *Pichia* sp., *Hansenula* sp., or *Kluyveromyces, Yarrowinia, Schizosaccharomyces* species or a species of *Saccharomyces*, including *Saccharomyces cerevisiae* or a species belonging to *Schizosaccharomyces* such as, for example, *S. pombe* species. A strain of the methylotrophic yeast species, *Pichia pastoris*, can be used as the host organism. Alternatively, the host organism can be a *Hansenula* species. Suitable host organisms among filamentous fungi include species of *Aspergillus*, e.g., *Aspergillus niger, Aspergillus oryzae, Aspergillus tubigensis, Aspergillus awamori*, or *Aspergillus nidulans*. Alternatively, strains of a *Fusarium* species, e.g., *Fusarium oxysporum* or of a *Rhizomucor* species such as *Rhizomucor miehei* can be used as the host organism. Other suitable strains include *Thermomyces* and *Mucor* species. In addition, *Trichoderma reesei* can be used as a host. A suitable procedure for transformation of *Aspergillus* host cells includes, for example, that described in EP 238023.

In a yet further aspect, a method of producing an AmyWDG195-related amylase is provided comprising cultivating a host cell as described above under conditions conducive to the production of the enzyme and recovering the enzyme from the cells and/or culture medium.

The medium used to cultivate the cells may be any conventional medium suitable for growing the host cell in question and obtaining expression of an AmyWDG195-related amylase. Suitable media and media components are available from commercial suppliers or may be prepared according to published recipes (e.g., as described in catalogues of the American Type Culture Collection).

In one aspect, an enzyme secreted from the host cells is used in a whole broth preparation. In the present methods, the preparation of a spent whole fermentation broth of a recombinant microorganism can be achieved using any cultivation method known in the art resulting in the expression of an alpha-amylase. Fermentation may, therefore, be understood as comprising shake flask cultivation, small- or large-scale fermentation (including continuous, batch, fed-batch, or solid state fermentations) in laboratory or industrial fermenters performed in a suitable medium and under conditions allowing the amylase to be expressed or isolated. The term "spent whole fermentation broth" is defined herein as unfractionated contents of fermentation material that includes culture medium, extracellular proteins (e.g., enzymes), and cellular biomass. It is understood that the term "spent whole fermentation broth" also encompasses cellular biomass that has been lysed or permeabilized using methods well known in the art.

An enzyme secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

An aspect contemplates the polynucleotide in a vector is operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions that allow expression of an AmyWDG195-related amylase. Expression of the enzymes may be constitutive such that they are continually produced, or inducible, requiring a stimulus to initiate expression. In the case of inducible expression, protein production can be initiated when required by, for example, addition of an inducer substance to the culture medium, for example dexamethasone or IPTG or Sopharose. Polypeptides can also be produced recombinantly in an in vitro cell-free system, such as the TnT™ (Promega) rabbit reticulocyte system.

An AmyWDG195-related amylase-expressing host also can be cultured in the appropriate medium for the host, under aerobic conditions. Shaking or a combination of agitation and aeration can be provided, with production occurring at the appropriate temperature for that host, e.g., from about 25° C. to about 75° C. (e.g., 30° C. to 45° C.), depending on the needs of the host and production of the desired AmyWDG195- related polypeptide. Culturing can occur from about 12 to about 100 hours or greater (and any hour value there between, e.g., from 24 to 72 hours). Typically, the culture broth is at a pH of about 5.5 to about 8.0, again depending on the culture conditions needed for the host relative to production of an AmyWDG195-related amylase.

In some embodiments, an AmyWDG195-related amylase is expressed in the presence of additional NaCl added to the media, as compared to, for example, minimal media. The minimal media used herein included about 50 mM NaCl in addition to a small amount contributed by other component. The addition of 1%, 2%, or even 3% salt resulted in a significant increase in the amount of AmyWDG195-related amylase produced. Previous studies have suggested that NaCl was important for AmyK38 activity but not expression.

An aspect of the composition and method is the expression of an AmyWDG195-related polypeptide in the presence of additional NaCl, which increases the yield of polypeptide that is expressed in host cells. In some embodiments, the amount of NaCl is about 1% and the increase in yield is at least 3, at least 6, and even at least 9-fold. In some embodiments, the amount of NaCl is about 2% and the increase in yield is at least 4, at least 8, at least 12, and even at least 16-fold. In some embodiments, the amount of NaCl is about 3% and the increase in yield is at least 5, at least 10, at least 15, at least 20, at least 25, at least 30, and even at least 35-fold.

Generally, according to the method, an expression vector containing a polynucleotide encoding a signal sequence linked to a polynucleotide encoding an AmyWDG195-related polypeptide is constructed and introduced into a host cell. The AmyWDG195-related polypeptide is then expressed in host cells using medium enriched for NaCl as described, wherein the signal peptide directs secretion of the AmyWDG195-related polypeptide and the additional salt increases the yield. Finally, the AmyWDG195-related polypeptide is recovered and purified as desired.

3.2 Materials and Methods for Protein Purification

Fermentation, separation, and concentration techniques are well known in the art and conventional methods can be used in order to prepare a concentrated AmyWDG195-related amylase-containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, ultrafiltration, centrifugation followed by ultra-filtration, extraction, or chromatography, or the like, are generally used.

It is desirable to concentrate an AmyWDG195-related amylase-containing solution in order to optimize recovery. Use of unconcentrated solutions requires increased incubation time in order to collect the purified enzyme precipitate.

The enzyme containing solution is concentrated using conventional concentration techniques until the desired enzyme level is obtained. Concentration of the enzyme containing solution may be achieved using any of the techniques discussed herein or otherwise known in the art. Exemplary methods of concentration include but are not limited to rotary vacuum filtration and/or ultrafiltration.

Concentration may be performed using e.g., a precipitation agent, such as a metal halide precipitation agent. Metal halide precipitation agents include but are not limited to alkali metal chlorides, alkali metal bromides and blends of two or more of these metal halides. Exemplary metal halides include sodium chloride, potassium chloride, sodium bromide, potassium bromide and blends of two or more of these metal halides. The metal halide precipitation agent, sodium chloride, can also be used as a preservative.

The metal halide precipitation agent is used in an amount effective to precipitate the AmyWDG195-related polypeptide. The selection of at least an effective amount and an optimum amount of metal halide effective to cause precipitation of the enzyme, as well as the conditions of the precipitation for maximum recovery including incubation time, pH, temperature and concentration of enzyme, will be readily apparent to one of ordinary skill in the art, after routine testing.

Generally, at least about 5% w/v (weight/volume) to about 25% w/v of metal halide is added to the concentrated enzyme solution, and usually at least 8% w/v. Generally, no more than about 25% w/v of metal halide is added to the concentrated enzyme solution and usually no more than about 20% w/v. The optimal concentration of the metal halide precipitation agent will depend, among others, on the nature of the specific AmyWDG195-related amylase and on its concentration in the concentrated enzyme solution.

Another alternative to effect precipitation of the enzyme is to use organic compounds. Exemplary organic compound precipitating agents include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously.

Generally, the organic precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitation agents can be, for example, linear or branched alkyl esters of 4-hydroxybenzoic acid, wherein the alkyl group contains from 1 to 10 carbon atoms, and blends of two or more of these organic compounds. Exemplary organic compounds are linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl esters of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are both amylase preservative agents. For further descriptions, see, e.g., U.S. Pat. No. 5,281,526.

Addition of the organic compound precipitation agent provides the advantage of high flexibility of the precipitation conditions with respect to pH, temperature, AmyWDG195-related polypeptide concentration, precipitation agent concentration, and time of incubation.

The organic compound precipitation agent is used in an amount effective to improve precipitation of the enzyme by means of the metal halide precipitation agent. The selection of at least an effective amount and an optimum amount of organic compound precipitation agent, as well as the conditions of the precipitation for maximum recovery including incubation time, pH, temperature and concentration of enzyme, will be readily apparent to one of ordinary skill in the art, in light of the present disclosure, after routine testing.

Generally, at least about 0.01% w/v of organic compound precipitation agent is added to the concentrated AmyWDG195-related polypeptide solution and usually at least about 0.02% w/v. Generally, no more than about 0.3% w/v of organic compound precipitation agent is added to the concentrated AmyWDG195-related polypeptide solution and usually no more than about 0.2% w/v.

The concentrated enzyme solution, containing the metal halide precipitation agent, and the organic compound precipitation agent, can be adjusted to a pH, which will, of necessity, depend on the enzyme to be purified. Generally, the pH is adjusted at a level near the isoelectric point of the amylase. The pH can be adjusted at a pH in a range from about 2.5 pH units below the isoelectric point (pI) up to about 2.5 pH units above the isoelectric point.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme is between about 1 to about 30 hours; usually it does not exceed about 25 hours. In the presence of the organic compound precipitation agent, the time of incubation can still be reduced to less about 10 hours and in most cases even about 6 hours.

Generally, the temperature during incubation is between about 4° C. and about 50° C. Usually, the method is carried out at a temperature between about 10° C. and about 45° C. (e.g., between about 20° C. and about 40° C.). The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration, or the like. Further purification of the purified enzyme precipitate can be obtained by washing the precipitate with water. For example, the purified enzyme precipitate is washed with water containing the metal halide precipitation agent, or with water containing the metal halide and the organic compound precipitation agents.

During fermentation, an AmyWDG195-related amylase accumulates in the culture broth. For the isolation and purification of the desired AmyWDG195-related amylase, the culture broth is centrifuged or filtered to eliminate cells, and the resulting cell-free liquid is used for enzyme purification. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme-active fraction. For further purification, a conventional procedure such as ion exchange chromatography may be used.

Purified enzymes are useful for laundry and cleaning applications. For example, they can be used in laundry detergents and spot removers. They can be made into a final product that is either liquid (solution, slurry) or solid (granular, powder).

A more specific example of purification, is described in Sumitani, J. et al. (2000) *Biochem. J.* 350: 477-484 and is briefly summarized here. The enzyme obtained from 4 liters of a *Streptomyces lividans* TK24 culture supernatant was treated with $(NH_4)_2SO_4$ at 80% saturation. The precipitate was recovered by centrifugation at 10,000×g (20 minutes and 4° C.) and re-dissolved in 20 mM Tris/HCl buffer (pH 7.0) containing 5 mM $CaCl_2$. The solubilized precipitate was then dialyzed against the same buffer. The dialyzed sample was then applied to a Sephacryl S-200 column, which had previously been equilibrated with 20 mM Tris/HCl buffer, (pH 7.0), 5 mM $CaCl_2$, and eluted at a linear flow rate of 7 cm/hr with the same buffer. Fractions from the column were collected and assessed for activity as judged by enzyme assay and SDS-PAGE. The protein was further purified as follows. A Toyopearl HW55 column (Tosoh Bioscience, Montgomeryville, Pa.; Cat. No. 19812) was equilibrated with 20 mM Tris/HCl buffer (pH 7.0) containing 5 mM $CaCl_2$ and 1.5 M $(NH_4)_2SO_4$. The enzyme was eluted with a linear gradient of 1.5 to 0 M $(NH_4)_2SO_4$ in 20 mM Tris/HCL buffer, pH 7.0 containing 5 mM $CaCl_2$. The active fractions were collected, and the enzyme precipitated with $(NH_4)_2SO_4$ at 80% saturation. The precipitate was recovered, re-dissolved, and dialyzed as described above. The dialyzed sample was then applied to a Mono Q HR5/5 column (Amersham Pharmacia; Cat. No. 17-5167-01) previously equilibrated with 20 mM Tris/HCl buffer (pH 7.0) containing 5 mM $CaCl_2$, at a flow rate of 60 mL/hour. The active fractions are collected and added to a 1.5 M $(NH_4)_2SO_4$ solution. The active enzyme fractions were re-chromatographed on a Toyopearl HW55 column, as before, to yield a homogeneous enzyme as determined by SDS-PAGE. See J. Sumitani et al., "New type of starch-binding domain: the direct repeat motif in the C-terminal region of *Bacillus* sp. no. 195 α-amylase contributes to starch binding and raw starch degrading," *Biochem. J.* 350: 477-484 (2000) for general discussion of the method and variations thereon.

For production scale recovery, an AmyWDG195-related amylase can be partially purified as generally described above by removing cells via flocculation with polymers. Alternatively, the enzyme can be purified by microfiltration followed by concentration by ultrafiltration using available membranes and equipment. However, for some applications, the enzyme does not need to be purified, and whole broth culture can be lysed and used without further treatment. The enzyme can then be processed, for example, into granules.

4. Cleaning Compositions

An aspect of the present compositions and methods is a cleaning composition that includes an AmyWDG195-related amylase as a component. An AmyWDG195-related amylase can be used as a component in detergent compositions for hand washing, laundry washing, dishwashing, and other hard-surface cleaning. Preferably, an AmyWDG195-related amylase is incorporated into detergents at or near a concentration conventionally used for amylase in detergents. For example, an AmyWDG195-related amylase may be added in amount corresponding to 0.00001-1 mg (calculated as pure enzyme protein) of α-amylase per liter of wash/diswash liquor. Exemplary formulations are provided herein, as exemplified by the following:

4.1 Laundry Detergent Composition

An AmyWDG195-related amylase may typically be a component of a detergent composition, as the only enzyme or with other enzymes including other amylolytic enzymes. As such, it may be included in the detergent composition in the form of a non-dusting granulate, a stabilized liquid, or a protected enzyme. Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in for example EP 238,216. Polyols have long been recognized as stabilizers of proteins, as well as improving protein solubility. See, e.g., Kaushik, J. K. et al. (2003) *J. Biol. Chem.* 278: 26458-65 and references cited therein; and Monica Conti, M. et al. (1997) *J. Chromatography A* 757: 237-245.

The detergent composition may be in any useful form, e.g., as powders, granules, pastes, or liquid. A liquid detergent may be aqueous, typically containing up to about 70% of water and 0% to about 30% of organic solvent. It may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as lipase, another amylolytic enzyme, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e. essentially free of detergent builder. The enzymes can be used in any composition compatible with the stability of the enzyme. Enzymes generally can be protected against deleterious components by known forms of encapsulation, for example, by granulation or sequestration in hydro gels. Enzymes, and specifically α-amylases, such as AmyWDG195 molecules, either with or without starch binding domains, can be used in a variety of compositions including laundry and dishwashing applications, surface cleaners, as well as in compositions for ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxyacids (e.g., the amide, imide, or sulfone type peroxyacids). The bleaching system can also be an enzymatic bleaching system, for example, perhydrolase, such as that described in International PCT Application WO 2005/056783.

The enzymes of the detergent composition may be stabilized using conventional stabilizing agents, e.g., a polyol such as propylene glycol or glycerol; a sugar or sugar alcohol; lactic acid; boric acid or a boric acid derivative such as, e.g., an aromatic borate ester; and the composition may be formulated as described in, e.g., WO 92/19709 and WO 92/19708.

The detergent may also contain other conventional detergent ingredients such as e.g., fabric conditioners including clays, foam boosters, suds suppressors, anti-corrosion agents, soil-suspending agents, anti-soil redeposition agents, dyes, bactericides, tarnish inhibitors, optical brighteners, or perfumes.

The pH (measured in aqueous solution at use concentration) is usually neutral or alkaline, e.g., pH about 7.0 to about 11.0.

Particular forms of detergent compositions comprising the AmyWDG195-related polypeptides can be formulated to include:

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate (e.g., $Na_2O$, $2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O$, $2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O$, $2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O$, $2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers such as, e.g., lauryl methacrylate/acrylic acid copolymer; molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O$, $2SiO_2$) about 1% to about 4%; zeolite (e.g., $NaAlSiO_4$) about 20% to about 40%; Sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O$, $2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer such as, e.g., lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3.4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contain a manganese catalyst. The manganese catalyst for example is one of the compounds described in Rage et al. (1994) Nature 369:637-639.

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

An AmyWDG195-related amylase may be incorporated in concentrations conventionally employed in detergents. It is at present contemplated that, in the detergent composition, the enzyme may be added in an amount corresponding to 0.00001-1.0 mg (calculated as pure enzyme protein) of AmyWDG195-related amylase per liter of wash liquor.

In another embodiment, other enzymes, such as 2,6-4-3-D-fructan hydrolase, can be incorporated in detergent compositions comprising an AmyWDG195-related amylase and used for removal/cleaning of biofilm present on household and/or industrial textile/laundry.

The detergent composition may for example be formulated as a hand (manual) or machine (automatic) laundry detergent composition, including a laundry additive composition suitable for pre-treatment of stained fabrics and a rinse added fabric softener composition, or be formulated as a detergent composition for use in general household hard surface cleaning operations, or be formulated for manual or automatic dishwashing operations.

In a specific aspect, the detergent composition can comprise 2,6-β-D-fructan hydrolase in addition to an AmyWDG195-related amylase, and one or more other cleaning enzymes, such as a protease, a lipase, a cutinase, a carbohydrase, a cellulase, a pectinase, a mannanase, an arabinase, a galactanase, another amylolytic enzyme, a xylanase, an oxidase, a laccase, and/or a peroxidase, and/or combinations thereof.

In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases:

Suitable proteases include those of animal, vegetable or microbial origin. Chemically modified or protein engineered mutants are included, as well as naturally processed proteins. The protease may be a serine protease or a metalloprotease, such as an alkaline microbial protease, a trypsin-like protease, or a chymotrypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Commercially available protease enzymes include but are not limited to: ALCALASE®, SAVINASE®, PRIMASE™, DURALASE™, ESPERASE®, and KANNASE™ (Novo Nordisk A/S); MAXATASE®, MAXACAL™, MAXAPEMT™, PROPERASE®, PURAFECT®, PURAFECT OXP™, FN2™, and FN3™ (Genencor International, Inc.).

Lipases:

Suitable lipases include those of bacterial or fungal origin. Chemically modified, proteolytically modified, or protein engineered mutants are included. Examples of useful lipases include but are not limited to lipases from *Humicola* (synonym *Thermomyces*), e.g., from *H. lanuginosa* (*T. lanuginosus*) (see e.g., EP 258068 and EP 305216), from *H. insolens* (see e.g., WO 96/13580); a *Pseudomonas* lipase (e.g., from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens*, *Pseudomonas* sp. strain SD 705 (see e.g., WO 95/06720 and WO 96/27002), *P. wisconsinensis* (see e.g., WO 96/12012); a *Bacillus* lipase (e.g., from *B. subtilis*; see e.g., Dartois et al. *Biochemica et Biophysica Acta*, 1131: 253-360 (1993)), *Geobacillus* (formerly *Bacillus*) stearothermophilus (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE ULTRA™ (Novo Nordisk A/S).

Polyesterases:

Suitable polyesterases can be included in the composition, such as those described in, for example, WO 01/34899 and WO 01/14629.

Amylases:

The compositions can be combined with other amylases, such as non-production enhanced α-amylase. These can include commercially available amylases, such as but not limited to DURAMYL®, TERMAMYL®, FUNGAMYL® and BAN™ (Novo Nordisk A/S); RAPIDASE® and PURASTAR® (from Genencor International, Inc.).

Cellulases:

Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed for example in U.S. Pat. Nos. 4,435, 307; 5,648,263; 5,691,178; 5,776,757; and WO 89/09259. Exemplary cellulases contemplated for use are those having color care benefit for the textile. Examples of such cellulases are cellulases described in for example EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include CELLUZYME® and CAREZYME® (Novo Nordisk A/S); CLAZINASE® and PURADAX HA® (Genencor International, Inc.); and KAC-500(B)™ (Kao Corporation).

Peroxidases/Oxidases:

Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include for example GUARDZYME™ (Novo Nordisk A/S).

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, etc. Exemplary detergent additive formulations include but are not limited to granulates, in particular non-dusting granulates, liquids, in particular stabilized liquids or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing about 30% or less water are also contemplated. The detergent composition can optionally comprise one or more surfactants, which may be non-ionic, including semi-polar and/or anionic and/or cationic and/or zwitterionic. The surfactants can be present in a wide range, from about 0.1% to about 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g., SKS-6 from Hoechst).

The detergent may comprise one or more polymers. Exemplary polymers include carboxymethylcellulose (CMC), poly(vinylpyrrolidone) (PVP), poly(ethylene glycol) (PEG), poly (vinyl alcohol) (PVA), poly(vinylpyridine-N-oxide), poly (vinylimidazole), polycarboxylates e.g., polyacrylates, maleic/acrylic acid copolymers), and lauryl methacrylate/acrylic acid copolymers.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

It is at present contemplated that in the detergent compositions, the AmyWDG195-related polypeptides may be added in an amount corresponding to about 0.01 to about 100 mg of enzyme protein per liter of wash liquor (e.g., about 0.05 to about 5.0 mg of enzyme protein per liter of wash liquor or 0.1 to about 1.0 mg of enzyme protein per liter of wash liquor).

4.2 Cleaning Compositions

In the detergent applications, an AmyWDG195-related amylase is usually used in a liquid composition containing propylene glycol. The enzyme is solubilized in for example in propylene glycol by mixing in a 25% volume/volume propylene glycol solution containing 10% calcium chloride.

An AmyWDG195-related amylase thereof discussed herein can be formulated in detergent compositions for use in cleaning dishes or other cleaning compositions. These can be powders, gels, or liquids. The compositions can comprise the enzyme alone, or with other amylolytic enzymes and/or with other cleaning enzymes or bleach activating enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

The detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxysulphonates.

Other suitable organic builders include the higher molecular weight polymers and co-polymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, optionally with a bleach precursor or as a peroxy acid compound. Typical examples of suitable peroxy bleach compounds are alkali metal perborates, both tetrahydrates and monohydrates, alkali metal percarbonates, persilicates, and perphosphates. Exemplary activator materials are TAED, and glycerol triacetate. Enzymatic bleach activation systems may also be present in the formulation, e.g., such as perborate or percarbonate, glycerol triacetate and perhydrolase (see, e.g., WO 2005/056783).

The cleaning composition may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester).

The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

Although the present compositions and methods have been described with reference to the details below, it would be understood that various modifications can be made.

4.3 Methods of Assessing Detergent Compositions

Numerous α-amylase cleaning assays exist. Exemplary description of testing cleaning includes the following.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate, egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The "smaller swatch" can also be made by applying a stain to a small piece of material. For example, the smaller swatch can be a stained piece of fabric ⅝" or 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of either metal, plastic, glass, ceramic, or other suitable material that is coated with the soil substrate. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis. A further microscreening assay can be to deliver and secure a swatch, for example an indigo dyed denim, to a well of a multi-well plate, and add particles such as sand or larger particles such as for example garnet sieved to include particle 6 to 8, or 9 gauge, and agitate the plate so as to cause abrasion of the swatch by the added particles. This assay has found use in the assessment of cellulases in stone washing applications. The effectiveness of the enzyme can be judged by either color release (e.g., released indigo is dissolved in dimethylsulfoxide and absorbance at $A_{600}$ nm is measured) to the reaction buffer or by reflectance measurements of the abraded swatch.

When, for example, untreated BMI (blood/milk/ink) swatches are washed in detergent without bleach, a large portion of the ink is released even without the help of a protease. Adding a protease leads to a small increase in ink release, which can be hard to quantify over the large background. The present compositions and methods provide a treatment protocol that allows one to control the degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk-Testgewebe GmbH, Krefeld Germany; or Center for Test Materials, Vlaardingen, The Netherlands) and/or can be made by the practitioner (Morris and Prato, *Textile Research Journal* 52(4): 280 286 (1982)). Other test swatches include but are not limited to blood/milk/ink (BMI) stain(s) on a cotton-containing fabric, a spinach stain on a cotton-containing fabric, or grass on a cotton-containing fabric, and chocolate/milk/soot on a cotton-containing fabric.

A BMI stain can be fixed to cotton with 0.0003% to 0.3% hydrogen peroxide. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see e.g., Cayot and Tainturier, Anal. Biochem. 249: 184-200 (1997)). However, if a detergent or an enzyme sample leads to the formation of unusually small peptide fragments (for example, from the presence of peptidases in the sample), then one will obtain a larger TNBS signal, i.e., more "noise".

Another means of measuring wash performance of blood/milk/ink or other stain is based on ink release. Proteolysis of protein on the swatches leads to the release of ink particles which can be quantified by measuring the absorbance of the wash liquor. The absorbance can be measured at any wavelength between 350 and 800 nm. The absorbance is measured at 410 nm or 620 nm. The wash liquor can also be examined to determine the wash performance on stains containing grass, spinach, gelatin or Coomassie stain. Exemplary wavelengths for these stains include 670 nm for spinach or grass and 620 nm for gelatin or Coomassie. For example, an aliquot of the wash liquor (typically 100-150 μL from a 96-well microplate, for example) is removed and placed in a cuvette or multiwell microplate. This is then placed in a spectrophotometer and the absorbance is read at an appropriate wavelength.

The system can also be used to determine an enhanced enzyme and/or detergent composition for dish washing, for example, using a blood/milk/ink stain on a suitable substrate such as cloth, plastic or ceramic.

In one aspect, the BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tested with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains.

The present application is organized into a number of sections for ease of reading; however, the reader will appreciate that statements made in one section may apply to other sections. In this manner, the headings used for different sections of the disclosure should not be construed as limiting.

In order to further illustrate the compositions and methods, and advantages thereof, the following specific examples are given with the understanding that they are illustrative rather than limiting.

EXAMPLES

Example 1

Identification of *Halomonas variabilis* WDG195 Alpha-Amylase from an Expression Library of *Halomonas variablis* WDG195

Strain WDG195 was obtained from Prof. Grant, University of Leicester, UK. This strain was isolated from soda soil on the shore of Mono Lake, Calif., USA. Partial sequencing of the 16S rRNA gene (429 bp) indicated that the strain belongs to the species *Halomonas variabilis*. The partial 16S rRNA gene sequence is shown in SEQ ID NO: 2.

Cells of *Halomonas variabilis* WDG195 were cultivated on an alkaline medium, for example using methods according to Duckworth et al., FEMS Microbiology Letters 19 (1996) 181-191. Genomic DNA (>4 μg) was prepared using MasterPure Gram Positive DNA purification Kit from Epicentre (http://www.epibio.com/item.asp?id=429), using the manufacturer's protocol (http://www.epibio.com/pdftechlit/209p1085.pdf). The resulting genomic DNA was used by Eurofins Medigenomix GmbH (Martinsried, Germany) for the construction of an expression library. Fragments of 3-5 kb were obtained by random shearing and the fragments were cloned into low copy number vector pRANGER-BTB3-Cat (Lucigen Corporation, Middleton, Wis. USA, DQ058731) (FIG. 1). The vector was first modified for TA shotgun cloning by Medigenomix.

Figure 2:
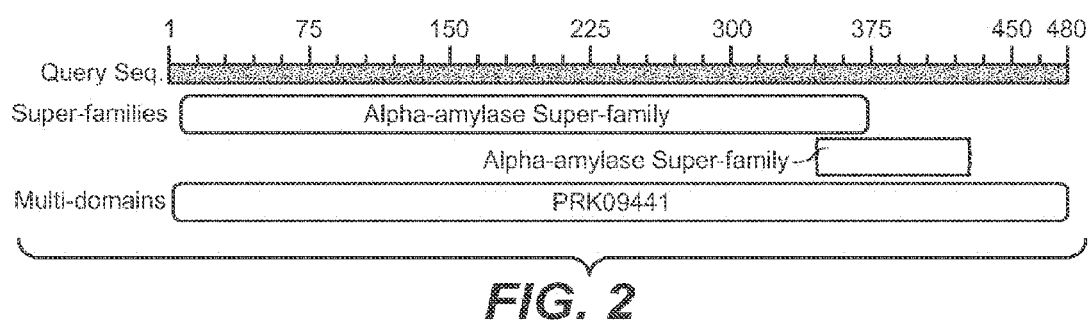
FIG. 2 shows the results of a BLAST search showing that AmyWDG195 belongs to the α-amylase superfamily.

Ligation mixtures were transformed into electrocompetent TOP10 *E. coli* cells (Invitrogen Carlsbad, Calif., USA) and plated on RBB plates. These agar plates contain 10 g yeast extract, 16 g tryptone, 5 g NaCl, 15 g agar, 25 mg chloramphenicol, and 5 g starch dyed with Remazol brilliant blue R (Fluka/Sigma-Aldrich Chemie B.V., Zwijndrecht, The Netherlands) per litter. An *E. coli* clone that formed a halo on the RBB plate, indicating the presence of an amylase gene that originates from *Halomonas variabilis* WG195, was selected for further analysis. The insert was sequenced by Baseclear (Leiden, The Netherlands) using the primers pRANGER-FW (SEQ ID NO: 3) and pRANGER-RV (SEQ ID NO: 4), which hybridize to the pRANGER vector. Based on this initial sequence analysis, the complete sequence of the amyWDG195 gene (SEQ ID NO: 9) was determined using four internal primers (SEQ ID NO: 5, 6, 7 and 8). The amyWDG195 gene encodes a precursor protein of 502 amino acids (SEQ ID NO: 10). The precursor protein consist of a signal peptide of 22 amino acids (SEQ ID NO: 11) and a mature portion of 480 amino acids (AmyWDG195, SEQ ID NO: 12). The results of a BLAST search performed through NCBI suggested that AmyWDG195 belongs to the alpha-amylase superfamily (FIG. 2), with its nearest neighbor being AmyK38 from *Bacillus* sp. KSM-K38, with which it shares 79% sequence identity.

Example 2

Protein Expression of *Halomonas variabilis* WDG195 Alpha-Amylase

To express AmyWDG195 amylase in *Bacillus subtilis*, an expression construct/plasmid was made based on the pHPLT vector, which contains the thermostable amylase LAT promoter (pLAT) and the LAT signal peptide (pre LAT) of *Bacillus licheniformis*, followed by PstI and HpaI restriction sites to facilitate cloning (FIG. 3; see, e.g., U.S. Pat. Nos. 5,871,550 and 6,562,612; U.S. Pat. Pub. No. 20060014265; and Solingen et al. (2001) *Extremophiles* 5:333-341).

*Halomonas* strainWDG195 genomic DNA was prepared from 1 ml cell pellet of an overnight culture (Tryptic Soy Broth at 37° C.) using the MasterPure Gram Positive DNA purification Kit from Epicentre (http://www.epibio.com/item.asp?id=429) according to the manufacturer's protocol (http://www.epibio.com/pdftechlit/209p1085.pdf). The amyWDG195 amylase gene was amplified from the genomic DNA sample by PCR performed on a MJ Research PTC-200 thermocycler with Phusion High Fidelity DNA polymerase (Finnzymes OY, Espoo, Finland) according to the instructions of the manufacturer (annealing temperature of 55° C.). The two primers used were: PstI-Amy195-1-Fw (SEQ ID NO: 13) and HpaI-Amy195-Rv (SEQ ID NO: 14).

The resulting PCR fragment was digested with restriction enzymes PstI and HpaI, and incubated with pHPLT DNA (50 ng/µl, also digested with PstI and HpaI) in the presence of T4 DNA ligase according to the instructions of the supplier (Roche Applied Science, Indianapolis, Ind., USA). The ligation mixture was transformed into *B. subtilis* strain BG6006, which is deleted for nine proteases (i.e., degUHy32,oppA, DspoII3501, amyE::xy1RPxy1AcomK-ermC, DaprE, DnprE, Depr, DispA, Dbpr, Dvpr, DwprA, Dmpr-ybfJ, DnprB) [see, e.g., U.S. Pat. Pub Nos. 20050202535 and 20020182734 (WO 02/14490)]. The transformation mixture was plated on Difco™ Heart Infusion Agar plates containing 10 mg/L neomycin and 0.5% starch dyed with Remazol brilliant blue R. A starch-halo-positive colony was selected and the presence of the AmyWDG195 amylase gene in pHPLT was confirmed using colony PCR and sequencing. For colony PCR, the transformed bacteria was resuspended in 100 µL of sterile water of which 1 µL was used in a PCR reaction containing Invitrogen Platinum Taq DNA Polymerase and two primers: pHPLT-F1 (SEQ ID NO: 15) and pHPLT-R1 (SEQ ID NO: 16).

PCR was performed at 95° C. for 2 minutes followed by 25 cycles at 95° C. for 0.5 minute, 55° C. for 1 minute, and 68° C. for 2 minutes. The reaction was stopped after a final incubation at 68° C. for 5 minutes. The PCR product was sequenced at BaseClear (Leiden, The Netherlands) using primers pHPLT-F1 (SEQ ID NO: 15), pHPLT-R1 (SEQ ID NO: 16) and Amy195.int.-Rv (SEQ ID NO: 17).

Sequence analysis confirmed the presence of the AmyWDG195 amylase coding sequence in the pHPLT-AmyWDG195 vector.

Growth of *B. subtilis* transformants harbouring the pHPLT-AmyWDG195 vector was performed in shake flasks containing 25 ml MBD medium (a MOPS based defined medium: Neidhardt et al. (1974) *J. Bacteriol.*, 119: 736-747) and 10 mg/L neomycin. This growth resulted in the production of secreted AmyWDG195 amylase with starch hydrolyzing activity. Adding additional NaCl to the growth medium increases the production of secreted and active AmyWDG195 protein, as shown in the following Table.

| Production Medium | Relative Amylase Expression |
|---|---|
| MBD | 1x |
| +1% NaCl | 9x |
| +2% NaCl | 16x |
| +3% NaCl | 35x |

Example 3

Identification, Cloning, and Expression of AmySWT282

An amylase (AmySWT282) similar to AmyWDG195 (~78% amino acid identity) was identified from the alkaliphilic *Bacillus* strain SWT282 (isolated on alkaline tomato puree agar from a sample provided by Dr. Dimitri Sorokin (Inst. of Microbiology, Moscow, Russia), which was collected from the Kalunda Steppe (north) around Karasuk in the Novosibirsk region of Russia). Initially, a small fragment of the AmySWT282 gene was amplified from genomic DNA of this strain using degenerate primers DVVMNH-Forward (5'-GAYGTNGTNATGAAYCAY-3'; SEQ ID NO: 25; encoding 128 possible amino acid sequences) and VTFVDNHD-Reverse (5'-TCRTGRTTITCIACRAANGTNAC-3'; SEQ ID NO: 26; encoding 256 possible amino acid sequences). 2 µL of genomic DNA template and 1 µM of each primer (final concentration) were combined with water to a final volume of 25 µL with a PCR bead (GE Healthcare). The cycling conditions were as follows: 95° C., 4'; 95° C. 1'; 50° C., 1'; 72° C., 1'30"; 72° C., 5'; 4° C. A short DNA fragment of roughly 700 bp was amplified (as visualized on a 1.2% agarase gel) and sequenced. The DNA sequence of this fragment is shown in FIG. 9 as SEQ ID NO: 18. A BlastX search proved that this fragment indeed encodes an alpha-amylase fragment.

To identify as much of the AmySWT282 amylase gene as possible, degenerate primers close to the N and C terminus of the predicted AmySWT282 amylase gene fragment were designed, in particular, a degenerate forward primer corresponding to the to N-terminal MMQ F/Y FEW motif (5'-ATGATGCARTWYTTYGARTGG-3'; SEQ ID NO: 27; encoding 32 possible amino acid sequences) and reverse primers corresponding to the C-terminal VTIN G/A DGWG E/N F motif (5'-AAITYICCCCAICCRTCNSCRTTNGT-NAC-3'; SEQ ID NO: 28) or NGGSVSVYVN motif (5'-TTIACRAAIACISWIACISWICCNCCRTT-3'; SEQ ID NO: 29) (FIG. 9). Degenerate PCR reactions were set up using the MMQFEW forward primer separately in combination with each of the reverse primers listed above. Two µL of genomic DNA template and 1 µM of each primer (final concentration) were combined with water to a final volume of 25 µl with a PCR bead (GE Healthcare). The cycling conditions were as follows: 95° C., 4', 95° C., 1'; 50° C., 1'; 72° C., 1'30"; 72° C., 5'; 4° C. A 2.5 µl sample of the PCR reaction was analyzed on a 1.2% agarose gel. The forward MMQFEW and reverse VTINGDGWGEF primers produced a 1.4 kb band on the gel.

The band was gel purified using Qiagen gel purification kit and the DNA was eluted in 35 µl of buffer EB. 4 µl of the purified fragment was cloned into the PCR2.1 TOPO® vector using a 30 min TOPO® cloning reaction (Invitrogen Corp., Carlsbad, Calif.) at room temp. 2.5 µl of the reaction was transformed into 50 µl of Top 10 chemically competent cells. After ice and heat shock, 250 µl of SOC media was added to the cells and sample shaken at 37° C. for 1 hour. After one hour, 200 µl of the cell suspension was plated on IPTG-X-gal plates containing 100 ppm carbenicillin and the plates were incubated at 37° C. overnight. 4 white colonies were picked from the X-gal plates and used for colony PCR with the TOPO F (5'-CACTTTATGCTTCCGGCTCGTATG-3'; SEQ ID NO: 40) and TOPO R primers (5'-TCGCCATTCAGGCT-GCGCAACTG-3; SEQ ID NO: 41). Three of the colonies produced the desired 1.7 kb band, which was sequenced with the TOPO seq F and R primers. This process yielded extended sequence information about the gene encoding the AmySWT282 gene.

To obtain more sequence information relating to the full-length amySWT282 gene, the following four primers were designed based on the extended sequence information. These primers were used in two different PCR reactions and designed for use with the Takara LA in vitro Cloning Kit (Takara Bio USA, Madison, Wis.).

```
N-Term SWT282 primer 2
                               (SEQ ID NO: 30)
5'-CTAAATCATACAAGTCATAGGCACCATAGCCGAC-3'

N-Term SWT282 primer 1
                               (SEQ ID NO: 31)
5'-GCAGCTCCTGCTTTGTGCCGTACTTCGTG-3'

C-term SWT282 primer 2
                               (SEQ ID NO: 32)
5'-GACCACTGGGATATCGTTGGTTGGACGAG-3'

C-term SWT282 primer 1
                               (SEQ ID NO: 33)
5'-CACGCACGGATTATTCTTACGGCACACAG-3'
```

Following the manufacturer's protocol AmySWT282 genomic DNA was digested with XbaI and ligated to the XbaI cassette. The first PCR reaction for the N terminal portion of the gene were carried out with primers 282 N3 (5'-TACGC-CGTTAAAATGGTACCAGTGCCAG-3'; SEQ ID NO: 36)+ kit primer C1, while the C terminal PCR reaction was performed using primers 282 C1 (5'-CACGCACGGATTATTCTTACGGCACACAG-3'; SEQ ID NO: 37)+kit primer C1. PCR products were confirmed on a gel, and then diluted $10^{-1}$, $10^{-2}$, and $10^{-4}$ before use as template for nested PCR reactions on the respective ends. The N-terminal nested PCR reaction used primer pair 282 N5 (5' ATTCACCTGCACCGCATCCACCGCTTCGG 3'; SEQ ID NO: 38)+kit primer C2, while the C terminal nested PCR used primer pair 282 C2 (5'-GACCACTGGGATATCGTTGGT-TGGACGAG-3'; SEQ ID NO: 39)+kit primer C2. The resulting PCR products were gel purified and ligated into the Topo TA vector, then transformed into 50 μl of Top 10 chemically competent cells. 4 colonies each were picked for PCR with primers Topo F and TOPO R (described, above) and the PCR products were sequenced. This resulted in new sequence information of the SWT282 amylase gene.

The last piece of sequence information of the amySWT282 gene was retrieved by directly sequencing genomic DNA of Bacillus strain SWT282 (Fidelity systems, Cessna Avenue, Gaithersburg, Md.), thereby completing the sequence of the amySWT282 gene. The full-length amySWT282 gene and AmySWT282 (precursor) protein sequences are shown as SEQ ID NOs: 19 and NO: 22, respectively. AmySWT282 has a signal peptide (SEQ ID NO: 21 and NO: 24), and is thus an extracellular protein. The mature AmySWT282 polypeptide has 479 amino acid residues (SEQ ID NO: 23) and is encoded by the polynucleotide of SEQ ID NO: 20. The mature AmySWT282 polypeptides showed moderate homology (<61% identity) to the α-amylases from Bacillus licheniformis, Geobacillus (formerly Bacillus) stearothermophilus, and Bacillus amyloliquefaciens.

Figure 6:
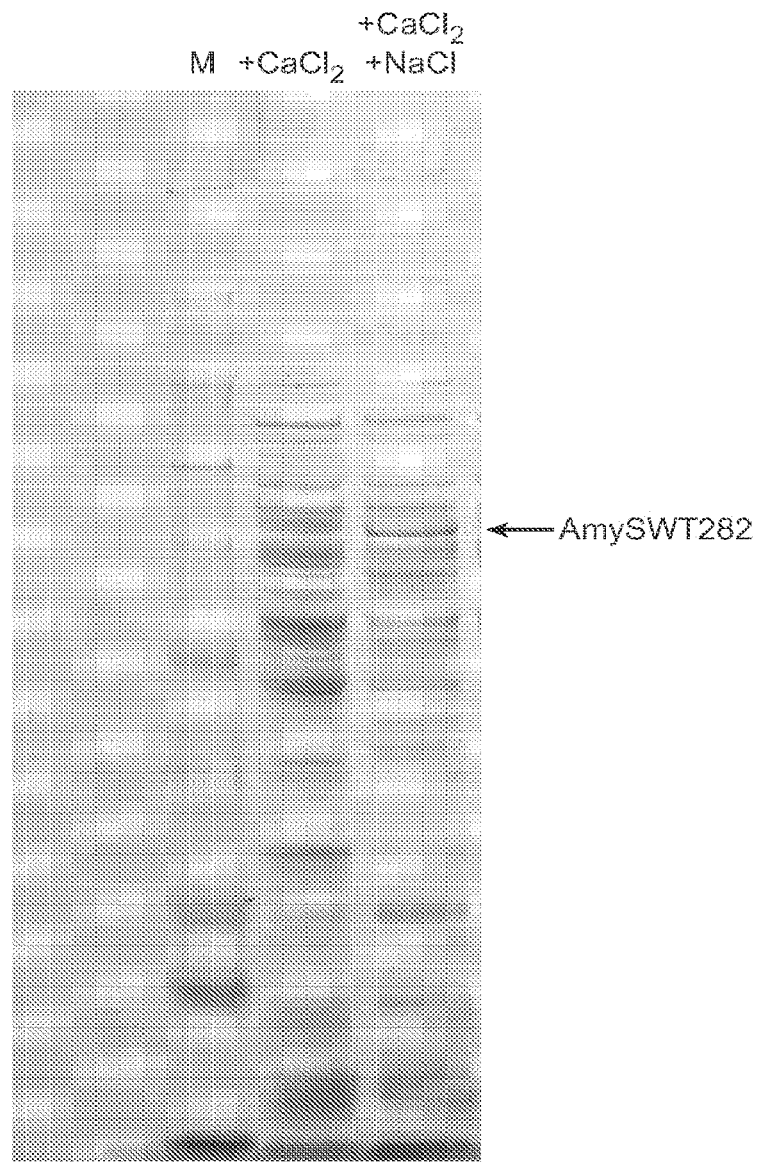
FIG. 6 is an image of a Coomassie-stained gel showing expression of AmySWT282.

The amySWT282 gene was cloned into the pHPLT B. subtilis expression vector as described for amyWDG195 in Example 2. A B. subtilis transformant harboring pHPLT-AmySWT282 was grown in shake flasks containing MBD medium with 10 mg/L neomycin, 20 mM extra $CaCl_2$, and with and without additional NaCl (3%). After 72 h growth, culture supernatants were analyzed by SDS-PAGE (FIG. 6). The addition of extra NaCl to the growth medium was necessary for production of AmySWT282, as observed for Amy-WDG195. In contrast, the addition of $CaCl_2$ showed no beneficial affect on the heterologous expression of AmySWT282.

Example 4

Assay for Cleaning

Culture supernatant from the pHPLT-AmyWDG195 vector transformed cells grown in MBD medium (Example 2) was analyzed for activity in a 96-well CS28-orange-dyed-rice-starch-soiled-fabric-swatch micro-applications cleaning assay. Using a fabric punch, ¼-inch discs were cut from CS28 colored rice starch stained fabric swatches. This starch includes a bound indicator dye to facilitate tracking (Test Fabrics Cat. No. CS-28; Center for Test Materials, Vlaardingen, The Netherlands). Two of these discs were placed in each well of a flat-bottomed 96-well assay plates.

For the α-amylase cleaning assay, a preselected buffer was added to the wells and equilibrated to a preselected temperature. For initial testing the buffers were 25 mM HEPES (pH 8.0) or 25 mM CAPS (pH 10.0), additionally containing 2 mM $CaCl_2$ and 0.0005% TWEEN 80. About 200 μL of buffer was added to different wells and allowed to equilibrate at 40° C. 10-20 μL of diluted culture supernatant solution (final amylase concentration of 0 ppm to 2 ppm) were added to selected wells and the plates incubated with shaking at 1150 rpm for 1 hour. Enzyme cleaning performance was based on the amount of enzyme-dependent color released into the wash liquor. Color release was quantified spectro-photometrically at 488 nm by the transfer of 100 μL final wash liquor to a fresh microtiter plate. The data were plotted with the aid of GRAFIT from Erithicus Software. The data points were fitted with the Langmuir isotherm-fitting algorithm, which takes the same form as the Michaelis-Menten fitting algorithm.

Figure 4:
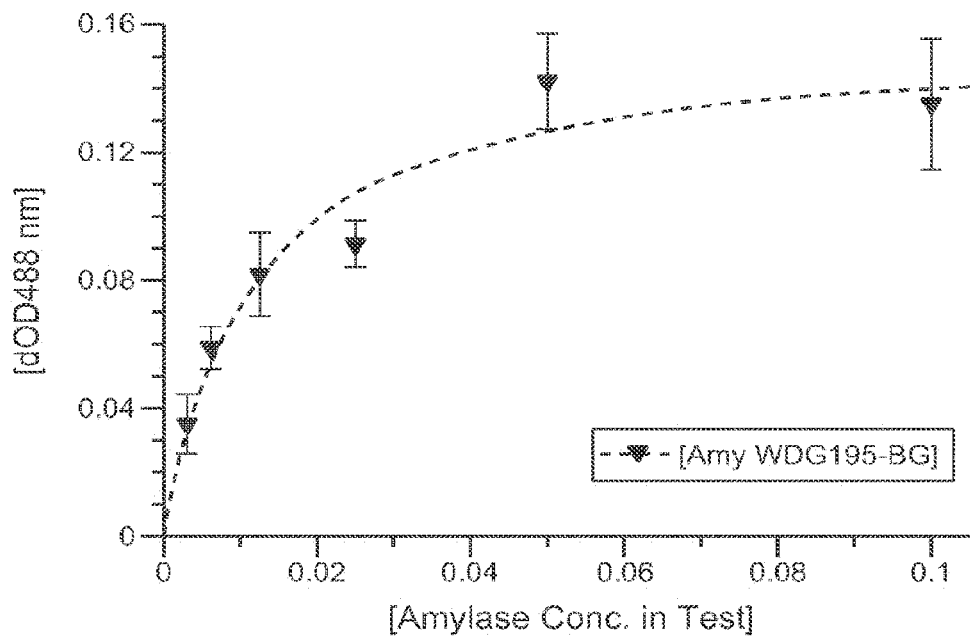
FIGS. 4 and 5 show the results of assays to evaluate cleaning performance.
Figure 5:
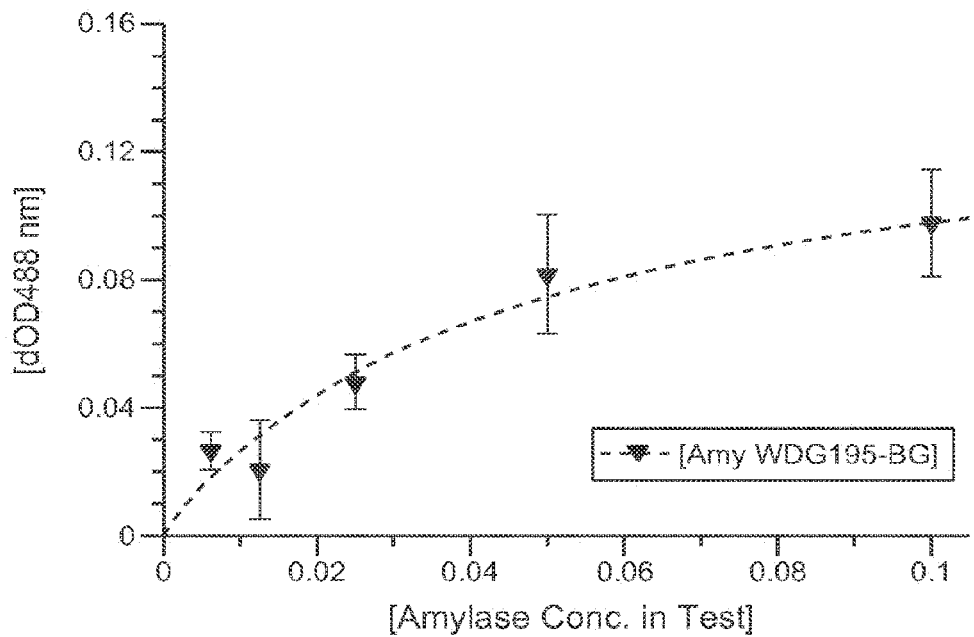

The results of this assay demonstrated that AmyWDG195 is highly efficient at removing starchy stains from textile swatches at 40° C. at pH 8.0, but slightly less efficient at pH 10.0 (FIGS. 4 and 5).

Example 5

Megazyme Assay for α-Amylase Activity

The α-amylase activity of AmyWDG195 culture supernatant from the transformed cells grown on MBD medium (Example 2) was determined using the Ceralpha method (Megazyme International, Ireland), which was modified for use in 96-well microtiter plate. 25 μl blocked p-nitrophenyl maltoheptaoside (=BPNPG7) substrate, 5.45 mg/mL (Amylase HR Reagent, Catalogue Number R-AMHR4Megazyme International) was added to each well and pre-equilibrated for 10 minutes at 25° C. Diluted culture supernatant (25 μl) was transferred into the wells and mixed with the substrate. Dilutions were made in 50 mM MOPS buffer pH 7.15, with 50 mM NaCl and 0.1 mM $CaCl_2$).

The plates were incubated with shaking at 650 rpm for 30 minutes in an incubator (iEMS, Labsystems), and the reaction was terminated by the addition of 50 μl 200 mM Boric acid/NaOH, pH 10.2, solution into each well. The absorbance at 400 nm indicated the level of α-amylase in the diluted sample.

All references cited herein are herein incorporated by reference in their entirety for all purposes.

---

What is claimed is:

1. An isolated polypeptide having α-amylase activity and having at least 90% amino acid sequence identity to SEQ ID NO: 12 or SEQ ID NO: 23 and including at least one of the following amino acid residues at the indicated amino acid position relative to SEQ ID NO: 12 or SEQ ID NO: 23, as determined by amino acid sequence alignment: E at position 3, E at position 20, M at position 25, N at position 26, L at position 40, D at position 68, E at position 82, Q at position 91, G at position 94, L at position 177, H at position 179, G at position 181, N at position 224, L at position 267, D at position 278, D at position 280, V at position 281, E at position 294, R at position 297, T at position 298, L at position 307, D at position 340, V at position 350, S at position 360, L at position 381, E at position 386, D at position 390, G at position 418, M at position 449, H at position 453, D at position 470, and Q at position 479.

2. The polypeptide of claim 1, including:
   (a) at least one of the following amino acid residues at the indicated amino acid position relative to SEQ ID NO: 12 or SEQ ID NO: 23: E at position 3, E at position 20, M at position 25, N at position 26, D at position 68, E at position 82, Q at position 91, G at position 94, L at position 177, H at position 179, G at position 181, N at position 224, D at position 278, D at position 280, V at position 281, E at position 294, R at position 297, T at position 298, D at position 340, V at position 350, S at position 360, E at position 386, D at position 390, G at position 418, M at position 449, H at position 453, D at position 470, and Q at position 479;
   (b) at least one of the following amino acid residues at the indicated amino acid position relative to SEQ ID NO: 12 or SEQ ID NO: 23: M at position 25, N at position 26, L at position 177, H at position 179, E at position 294, T at position 298, and M at position 449;
   (c) at least one of the following combinations of amino acid residues at the indicated amino acid position relative to SEQ ID NO: 12 or SEQ ID NO: 23: M at position 25 and N at position 26, optionally with E at position 20; Q at position 91 and G at position 94; L at position 177, H at position 179, and G at position 181; D at position 280 and V at position 281, optionally with D at position 278; R at position 297 and T at position 298, optionally with E at position 294; E at position 386 and D at position 390, optionally with L at position 381; and M at position 449 and H at position 453;
   (d) at least 30 glutamate residues;
   (e) at least one of the following amino acid residues at the indicated amino acid position relative to SEQ ID NO: 12 or SEQ ID NO: 23: N at position 104, D at position 194, N at position 200, and H at position 235;
   (f) at least one of the following amino acid residues at the indicated amino acid position relative to SEQ ID NO: 12 or SEQ ID NO: 23: Y at position 302, G at position 300, N at position 427, D at position 404, and W at position 403;
   (g) at least one of the following amino acid residues at the indicated amino acid position relative to SEQ ID NO: 12 or SEQ ID NO: 23: N at position 289, V at position 324, D at position 325, and S at position 337; or
   (h) the following amino acid residue at the indicated amino acid position relative to SEQ ID NO: 12 or SEQ ID NO: 23: L at position 197.

3. The polypeptide of claim 1, wherein the activity is independent of calcium.

4. A cultured cell material comprising a polypeptide of claim 1.

5. A cleaning composition comprising the polypeptide of claim 1.

6. The polypeptide of claim 1, wherein the polypeptide is a variant polypeptide that includes a man-made substitution, insertion, or deletion at one or more amino acid positions.

7. The polypeptide of claim 2, wherein the polypeptide is a variant polypeptide that includes a man-made substitution, insertion, or deletion at one or more amino acid positions.

8. The polypeptide of claim 3, wherein the polypeptide is a variant polypeptide that includes a man-made substitution, insertion, or deletion at one or more amino acid positions.

9. A cultured cell material comprising a polypeptide of claim 6.

10. A cleaning composition comprising the polypeptide of claim 6.

* * * * *